United States Patent
Tanino et al.

(10) Patent No.: US 12,351,804 B2
(45) Date of Patent: Jul. 8, 2025

(54) PRODUCTION METHOD FOR BIFURCATED LIPID-LINKED OLIGONUCLEOTIDE, AND INTERMEDIATE

(71) Applicant: Shionogi & Co., Ltd., Osaka (JP)

(72) Inventors: Tetsuya Tanino, Osaka (JP); Mitsuaki Sekiguchi, Hyogo (JP); Shunsuke Ochi, Hyogo (JP); Nobuaki Fukui, Hyogo (JP)

(73) Assignee: Shionogi & Co., Ltd., Osaka (JP)

( * ) Notice: Subject to any disclaimer, the term of this patent is extended or adjusted under 35 U.S.C. 154(b) by 887 days.

(21) Appl. No.: 17/616,413

(22) PCT Filed: Jun. 2, 2020

(86) PCT No.: PCT/JP2020/021676
§ 371 (c)(1),
(2) Date: Dec. 3, 2021

(87) PCT Pub. No.: WO2020/246443
PCT Pub. Date: Dec. 10, 2020

(65) Prior Publication Data
US 2022/0267771 A1    Aug. 25, 2022

(30) Foreign Application Priority Data

Jun. 3, 2019 (JP) ................................ 2019-103903

(51) Int. Cl.
| | | |
|---|---|---|
| A61K 39/00 | (2006.01) | |
| A61K 39/12 | (2006.01) | |
| A61K 39/39 | (2006.01) | |
| A61P 31/04 | (2006.01) | |
| A61P 35/00 | (2006.01) | |
| C07F 9/572 | (2006.01) | |
| C12N 15/117 | (2010.01) | |

(52) U.S. Cl.
CPC .......... *C12N 15/117* (2013.01); *C07F 9/5728* (2013.01); *C12N 2310/17* (2013.01); *C12N 2310/315* (2013.01); *C12N 2310/351* (2013.01)

(58) Field of Classification Search
CPC .... A61K 2039/545; A61K 2039/55561; A61K 39/39; A61K 2039/55566; A61K 2039/70
See application file for complete search history.

(56) References Cited

U.S. PATENT DOCUMENTS

2018/0264105 A1    9/2018 Kugimiya et al.

FOREIGN PATENT DOCUMENTS

| EP | 3 603 648 | 2/2020 |
|---|---|---|
| JP | 2015-514108 | 5/2015 |
| WO | 2010/071852 | 6/2010 |
| WO | 2013/151771 | 10/2013 |
| WO | 2015/012912 | 1/2015 |
| WO | 2017/057540 | 4/2017 |
| WO | 2018/179172 | 10/2018 |
| WO | 2018/181428 | 10/2018 |

OTHER PUBLICATIONS

International Search Report issued Sep. 1, 2020 in International (PCT) Application No. PCT/JP2020/021676.
Liu et al., "Membrane Anchored Immunostimulatory Oligonucleotides for In Vivo Cell Modification and Localized Immunotherapy", Angew. Chem. International Edition, 2011, vol. 50, No. 31, pp. 7052-7055.
Liu et al., "DNA-Based Micelles: Synthesis, Micellar Properties and Size-Dependent Cell Permeability", Chemistry A European Journal, 2010, vol. 16, No. 12, pp. 3791-3797.
Nikan et al., "Synthesis and Evaluation of Parenchymal Retention and Efficacy of a Metabolically Stable O-Phosphocholine-N-docosahexaenoyl-$_L$-serine siRNA Conjugate in Mouse Brain", Bioconjugate Chem. 2017, vol. 28, No. 6, pp. 1758-1766.
Biscans et al., "The valency of fatty acid conjugates impacts siRNA pharmacokinetics, distribution, and efficacy in vivo", Journal of Controlled Release, 2019, vol. 302, pp. 116-125.
Written Opinion and International Preliminary Report on Patentability issued Dec. 7, 2021 in corresponding Application No. PCT/JP2020/021676.

*Primary Examiner* — Barry A Chestnut
(74) *Attorney, Agent, or Firm* — Wenderoth, Lind & Ponack, L.L.P.

(57) ABSTRACT

Provided are production methods capable of controlling quality of a bifurcated lipid-linked oligonucleotide, and intermediates which is useful for the production method, has good stability, and is easy to manage and analyze. Specifically, it is a method for producing a bifurcated lipid-linked oligonucleotide including a step of reacting a compound of formula (II):

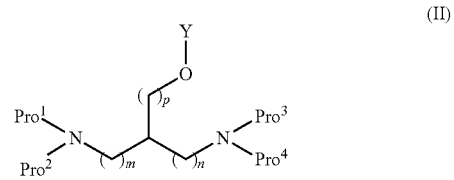

wherein $Pro^1$ to $Pro^4$ are each independently a protecting group;

$Pro^1$ and $Pro^2$ or $Pro^3$ and $Pro^4$ may be taken together to form a protecting group;

m, n and p are each independently an integer of 0 to 5; and

Y is a group of a formula: $-P(OC_2H_4CN)(N(i-Pr)_2)$, or the like, with an oligonucleotide.

14 Claims, No Drawings
Specification includes a Sequence Listing.

PRODUCTION METHOD FOR BIFURCATED LIPID-LINKED OLIGONUCLEOTIDE, AND INTERMEDIATE

TECHNICAL FIELD

The present invention relates to methods for producing a bifurcated lipid-linked oligonucleotide. Further, the present invention relates to intermediates useful for the production method.

BACKGROUND ART

Patent Document 1 describes an immunostimulatory CpG oligonucleotide to which a diacyl lipid (that is, bifurcated lipid) is linked. Moreover, a method for synthesizing a diacyl lipid phosphoramidite and a method for synthesizing a diacyl lipid-linked oligonucleotide are described in Example 1.

Patent Documents 2 and 3 describe diacyl lipid-linked double-stranded oligonucleotides exhibiting immunostimulatory activity. Further, these documents describe a method for synthesizing an amidite having a diacyl lipid in 1-1), 1-2) and 3) of A) of Example 1, and a method for synthesizing diacyl lipid-linked oligonucleotide in C).

Patent Document 4 describes a complex in which one bifurcated lipid containing two chains composed of alkyl via an amide at a terminal is linked to an oligonucleotide containing a nucleic acid drug such as an antisense oligonucleotide, siRNA, or microRNA (that is, a bifurcated lipid-linked oligonucleotide). Furthermore, Patent Document 4 describes a method for synthesizing an amidite in which a bifurcated lipid is linked in 1) of A) of Example 1, and a method for synthesizing a bifurcated lipid-linked oligonucleotide in C).

PRIOR ART REFERENCES

Patent Documents

[Patent Document 1] International Publication WO 2013/151771 A
[Patent Document 2] International Publication WO 2017/057540 A
[Patent Document 3] International Publication WO 2018/179172 A
[Patent Document 4] International Publication WO 2018/181428 A

SUMMARY OF THE INVENTION

Problems to be Solved by the Invention

An object of the present invention is to provide a production method capable of controlling quality of a bifurcated lipid-linked oligonucleotide, and intermediates which are useful for the production method, have good stability, and are easy to manage and analyze.

Means For Solving the Problem

Patent Documents 1 to 4 describe a method for obtaining a bifurcated lipid-linked double-stranded oligonucleotide by introducing an intermediate (amidite) having both a diacyl lipid (bifurcated lipid) and a linker unit into an oligonucleotide in a solid phase. The present inventors have found that in this method, dimers of the oligonucleotide are generated, and condensation efficiency between the amidite and the oligonucleotide is poor. In order to overcome this problem, as a result of intensive studies, the present inventors have found that by introducing a lipid after synthesizing an oligonucleotide, using an amidite in which two hydrogen atoms linked to a nitrogen atom to which an acyl lipid is to be introduced are substituted with protecting groups (amidite of the present invention) as an intermediate, generation of dimers is suppressed, condensation efficiency between the amidite and the oligonucleotide is improved, and a bifurcated lipid-linked oligonucleotide can be produced.

The present inventors have further found problems in quality control that compound 4-18 described in Patent Documents 2 and 3 (compound 5-18 described in Patent Document 4, comparative compound in Examples of the present application), which is an intermediate of the synthesis method described in Patent Documents 2 to 4, (a) has poor crystallinity and powder X-ray diffraction thereof is amorphous, (b) does not have an absorption band in a practical wavelength range in analysis using a general UV detector, and (c) is unstable even at −20° C. and decomposition over time was observed. Furthermore, the present inventors have found a problem that (d) efficiency of bifurcated lipid-linked oligonucleotide synthesis is relatively poor when the comparative compound is used.

On the other hand, as described in Example 2 below, (a') compound 5 which is the amidite (intermediate) of the present invention had good crystallinity. Therefore, purification operation by crystallization was easy, and the compound 5 could be obtained with a purity sufficiently better than that of the comparative compound. (b') Since the compound 5 has a UV absorption band generally considered to be derived from a phthaloyl group, analysis of purity and control and management of amount of impurities were easy. (c') No decomposition of the compound 5 was observed even at 40° C. for 50 days. As a result, it was possible to ensure quality of oligonucleotide by using the compound 5 that was quality controlled by liquid chromatography equipped with a UV detector as a raw material of the oligonucleotide. Further, (d') when the compound 5 was used, efficiency of bifurcated lipid-linked oligonucleotide synthesis was improved as compared to conventional methods described in Patent Documents 1 to 4.

The present inventors have attempted synthesis of an oligonucleotide to which a diacyl lipid is linked, using an amidite in which only one hydrogen atom linked to a nitrogen atom to which an acyl lipid is to be introduced is substituted with a protecting group. Using each of eight kinds of protecting groups, it was attempted from synthesis of amidite to synthesis of oligonucleotide in the same manner as in Example 1 below. However, there were problems that synthesis of amidite did not proceed, amidite was unstable and gradually decomposed, a condensation reaction between oligonucleotide and amidite proceeded, but the protecting group applied to amidite could not be deprotected, and the like. That is, the present inventors have found that the amidite of the present invention (a compound of the following formula (II) or its salt, particularly preferably a compound of the following formula (I) or its salt) is very excellent as an intermediate used in an efficient method for synthesizing a high-quality bifurcated lipid-linked oligonucleotide, as compared with an amidite in which only one hydrogen atom linked to a nitrogen atom to which an acyl lipid is to be introduced is substituted with a protecting group.

Moreover, as a result of intensive studies, the present inventors have found that when introducing the compound 5 into an oligonucleotide by a solid phase synthesis method to obtain compound 7, then cutting out from a solid phase carrier and performing deprotection to obtain compound 8, it is preferable to protect an amino group of cytosine in a sequence of the oligonucleotide with an acetyl group, and use n-butylamine or benzylamine as a cleavage reagent and a deprotecting agent. That is, the present inventors have found that both protecting groups (a protecting group of amino group of adenine, guanine or cytosine and a protecting group of hydroxy group of phosphoric acid) in the sequence of the oligonucleotide and a phthaloyl group can be efficiently removed without causing a side reaction, and a target bifurcated lipid-linked oligonucleotide is obtained. That is, it has been suggested that a condition of using butylamine and/or benzylamine as the cleavage reagent and the deprotecting agent of the present invention is particularly excellent as a method for synthesizing a high-quality bifurcated lipid-linked oligonucleotide as compared with other conditions.

Further, as a result of intensive studies, the present inventors have found that amines such as alkylamine used in the cut out from the solid phase carrier and deprotection step are factors that inhibit an acylation reaction, but residual amount of amines can be reduced by washing the compound 8 with methyl tert-butyl ether, which is an organic solvent. Furthermore, it has been found that when benzylamine is used in the cut out from the solid phase carrier and deprotection step, the residue can be tracked and managed by UV detection, and thus robustness with respect to progress of the acylation reaction is improved.

That is, the present invention relates to the following.

(1) A compound of formula (I):

[Formula 1]

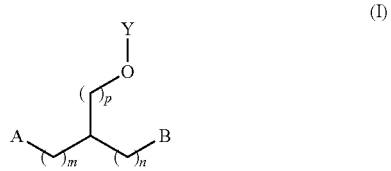

(I)

wherein
A and B are each independently

[Formula 2]

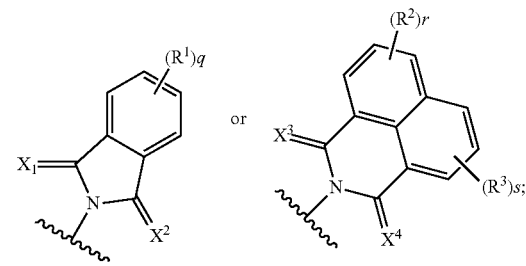

$X^1$, $X^2$, $X^3$, and $X^4$ are each independently O or S;
q are each independently an integer of 0 to 4;
r and s are each independently an integer of 0 to 3;
$R^1$, $R^2$, and $R^3$ are each independently halogen, hydroxy, substituted or unsubstituted alkyl, substituted or unsubstituted alkenyl, or substituted or unsubstituted alkynyl;
provided that $R^1$ of $(R^1)q$, $R^2$ of $(R^2)r$, and $R^3$ of $(R^3)s$ may be the same or different; and
m, n and p are each independently an integer of 0 to 5; and
Y is
a group of formula (Y-1): —$P(OR^4)(N(R^5)_2)$, wherein $R^4$ is substituted or unsubstituted alkyl, and $R^5$ are each independently substituted or unsubstituted alkyl,
a group of formula (Y-2): —$P(=R^6)(OR^7)_2$, wherein $R^6$ is O or S, and $R^7$ are each independently a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or
a group of formula (Y-3): —$P(=R^8)H(OR^9)$, wherein $R^8$ is O or S, and $R^9$ is a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl,
or its salt.

(2) The compound or its salt according to (1), wherein A and B are each independently

[Formula 3]

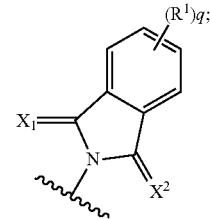

$X^1$ and $X^2$ are O, and
Y is a group of the formula (Y-1).

(3) The compound or its salt according to (1) or (2), wherein the compound is of the following formula.

[Formula 4]

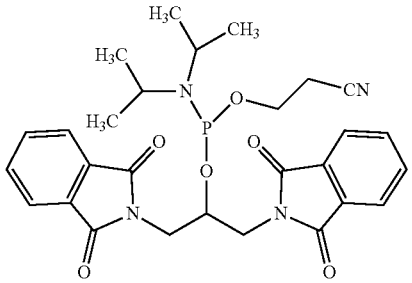

Note that the above (1) to (3) are useful intermediates that can be used as a compound of formula (II) in a production method according to any one of the following (4) to (10).

(4) A method for producing a compound of formula (VII):

[Formula 10]

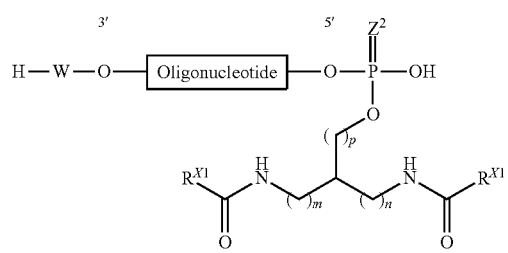

(VII)

wherein

Oligonucleotide means an oligonucleotide, 3' means a 3' end of the oligonucleotide, and 5' means a 5' end of the oligonucleotide.

W is a single bond or a compound of a formula:

[Formula 7]

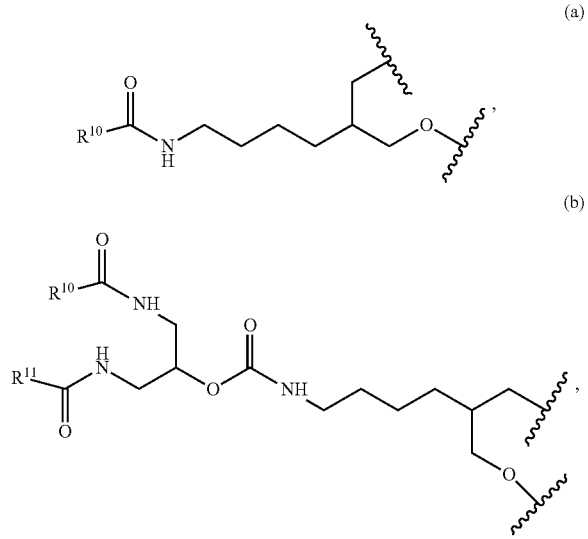

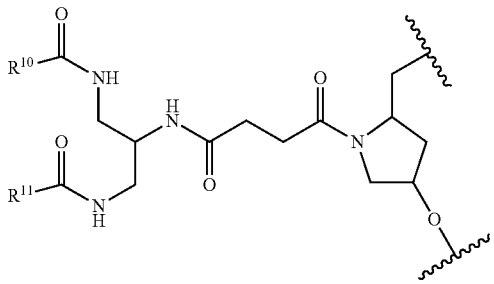

wherein $Z^1$ is O or S;

$R^{10}$ and $R^{11}$ are each independently alkyl or alkenyl;

terminal alkylene in the formula is bonded to oxygen at the 3' end of the oligonucleotide, and a terminal oxygen atom in the formula is bonded to a solid phase carrier;

$Z^2$ is

O or S when Y in formula (II) is a group of formula (Y-1), $R^6$ when Y in formula (II) is a group of formula (Y-2), and $R^8$ when Y in formula (II) is a group of formula (Y-3); and m, n and p are each independently an integer of 0 to 5; and $R^{X1}$ is alkyl or alkenyl, comprising steps of:

reacting a compound of formula (II):

[Formula 5]

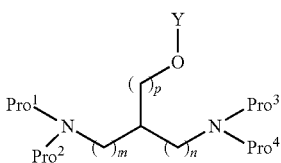

(II)

wherein $Pro^1$, $Pro^2$, $Pro^3$ and $Pro^4$ are each independently a protecting group;

$Pro^1$ and $Pro^2$ or $Pro^3$ and $Pro^4$ may be taken together to form a protecting group;

m, n and p have the same meaning as described above; and

Y is a group of formula (Y-1): —P(OR$^4$)(N(R$^5$)$_2$), wherein $R^4$ is substituted or unsubstituted alkyl, and $R^5$ are each independently substituted or unsubstituted alkyl, a group of formula (Y-2): —P(=R$^6$)(OR$^7$)$_2$, wherein $R^6$ is O or S, and $R^7$ are each independently a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or a group of formula (Y-3): —P(=R$^8$)H(OR$^9$), wherein $R^8$ is O or S, and $R^9$ is a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, with an olivonucleotide of formula (III):

[Formula 6]

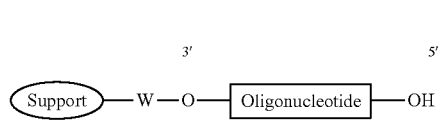
(III)

wherein Support means a solid phase carrier, and Oligonucleotide, 3', 5', and W have the same meaning as described above, to obtain a compound of formula (IV):

[Formula 8]

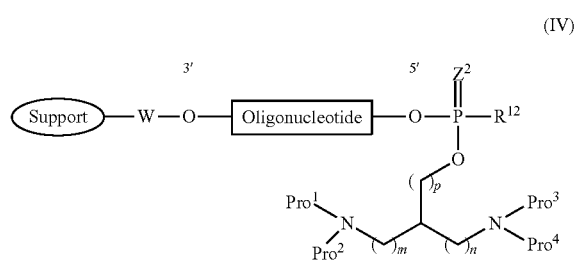
(IV)

wherein $R^{12}$ is $OR^4$ when Y in formula (II) is a group of formula (Y-1), $OR^7$ when Y in formula (II) is a group of formula (Y-2), and $OR^9$ when Y in formula (II) is a group of formula (Y-3); and Support, Oligonucleotide, 3', 5', W, $Z^2$, $Pro^1$, $Pro^2$, $Pro^3$, $Pro^4$, m, n, and p have the same meaning as described above, deprotecting a protecting group in the compound of formula (IV) and cutting out from a solid phase carrier, in the presence of a cleavage reagent and a deprotecting agent, to obtain a compound of formula (V):

[Formula 9]

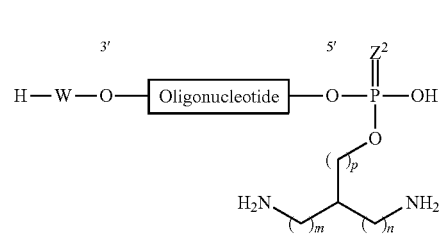
(V)

wherein each symbol has the same meaning as described above, and when W is any of the groups of the formulae (a) to (d), a terminal oxygen atom in the formulae (a) to (d) is bonded to a hydrogen atom; and reacting a compound of formula (VI): $R^{X1}$—C (=O)-$L^1$, wherein $R^{X1}$ has the same meaning as described above, and $L^1$ is OH or a leaving group with the compound of formula (V).

(5) A method for producing a compound of formula (X):

[Formula 17]

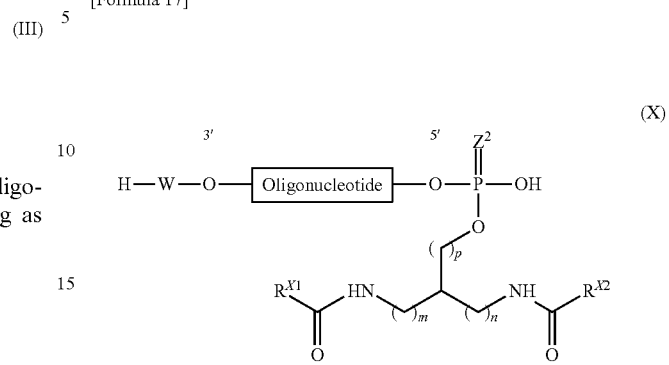
(X)

wherein

Oligonucleotide means an oligonucleotide, 3' means a 3' end of the oligonucleotide, and 5' means a 5' end of the oligonucleotide.

W is a single bond or a compound of a formula:

[Formula 13]

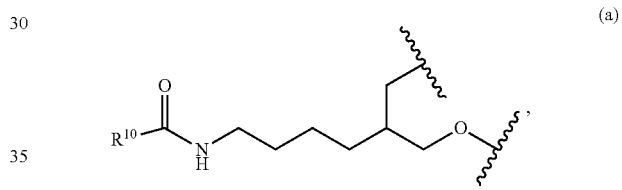
(a)

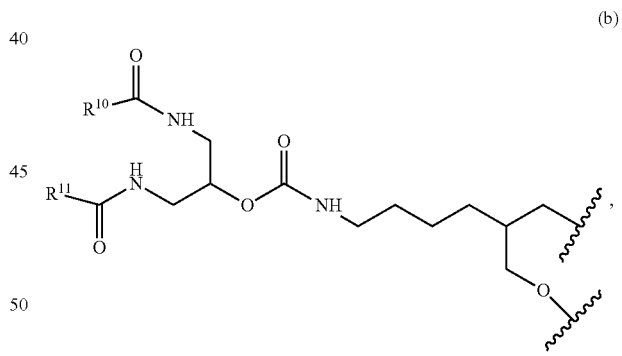
(b)

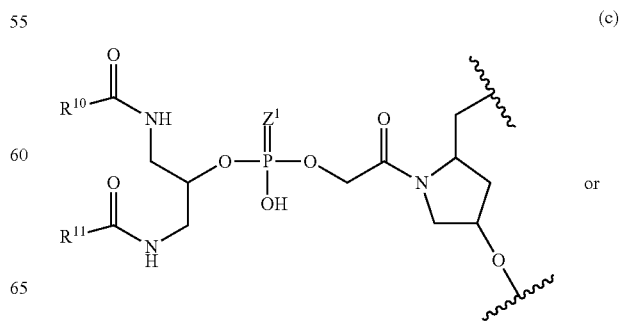
(c) or

-continued

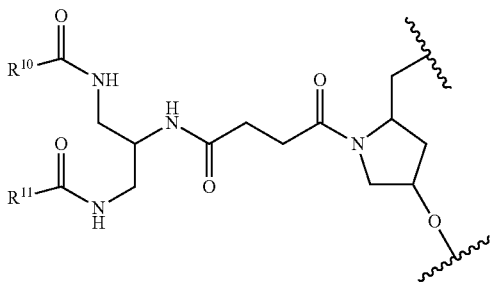
(d)

wherein $Z^1$ is O or S;
$R^{10}$ and $R^{11}$ are each independently alkyl or alkenyl;
terminal alkylene in the formula is bonded to oxygen at the 3' end of the oligonucleotide, and a terminal oxygen atom in the formula is bonded to a solid phase carrier;
$Z^2$ is
O or S when Y in formula (II) is a group of formula (Y-1),
$R^6$ when Y in formula (II) is a group of formula (Y-2), and
$R^8$ when Y in formula (II) is a group of formula (Y-3); and
m, n and p are each independently an integer of 0 to 5;
$R^{X1}$ is alkyl or alkenyl; and
$R^{X2}$ is alkyl or alkenyl;
comprising steps of reacting a compound of formula (II):

[Formula 11]

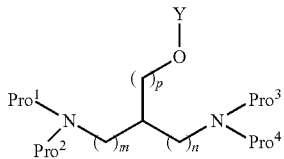
(II)

wherein
$Pro^1$, $Pro^2$, $Pro^3$ and $Pro^4$ are each independently a protecting group;
$Pro^1$ and $Pro^2$ or $Pro^3$ and $Pro^4$ may be taken together to form a protecting group;
m, n and p have the same meaning as described above;
Y is
a group of formula (Y-1): —P(OR⁴)(N(R⁵)₂), wherein $R^4$ is substituted or unsubstituted alkyl, and $R^5$ are each independently substituted or unsubstituted alkyl,
a group of formula (Y-2): —P(=R⁶)(OR⁷)₂, wherein $R^6$ is O or S, and $R^7$ are each independently a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or
a group of formula (Y-3): —P(=R⁸)H(OR⁹), wherein $R^8$ is O or S, and $R^9$ is a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl,
with an oligonucleotide of formula (III):

[Formula 12]

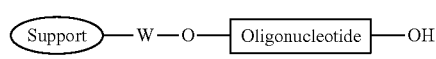
(III)

wherein Support means a solid phase carrier, and Oligonucleotide, 3', 5', and W have the same meaning as described above,
to obtain a compound of formula (IV):

[Formula 14]

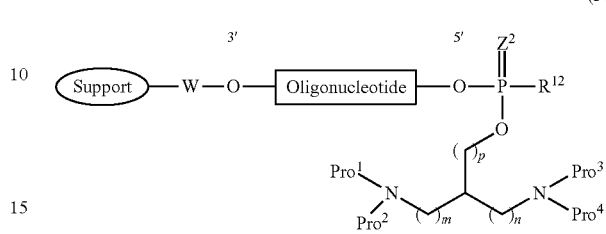
(IV)

wherein
$R^{12}$ is
$OR^4$ when Y in formula (II) is a group of formula (Y-1),
$OR^7$ when Y in formula (II) is a group of formula (Y-2), and
$OR^9$ when Y in formula (II) is a group of formula (Y-3); and
Support, Oligonucleotide, 3', 5', W, $Z^2$, $Pro^1$, $Pro^2$, $Pro^3$, $Pro^4$, m, n, and p have the same meaning as described above,
deprotecting a protecting group in the compound of formula (IV) and cutting out from a solid phase carrier, in the presence of a cleavage reagent and a deprotecting agent,
to obtain a compound of formula (V):

[Formula 15]

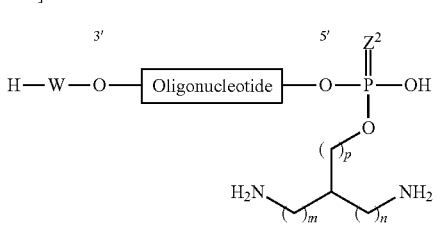
(V)

wherein each symbol has the same meaning as described above, and when W is any of the groups of the formulae (a) to (d), a terminal oxygen atom in the formulae (a) to (d) is bonded to a hydrogen atom;
reacting a compound of formula (VI): $R^{X1}$—C(=O)-L¹, wherein $R^{X1}$ has the same meaning as described above, and $L^1$ is OH or a leaving group
with the compound of formula (V),
to obtain a compound of formula (VIII):

[Formula 16]

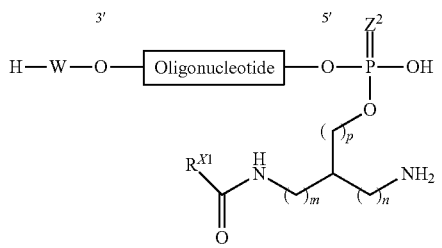
(VIII)

wherein each symbol has the same meaning as described above; and reacting a compound of formula (IX): $R^{X2}$—C(=O)-$L^2$, wherein $R^{X2}$ has the same meaning as described above, and $L^2$ is OH or a leaving group
with the compound of formula (VIII).
(6) The method according to (5), characterized in that $R^{X1}$ is C8 to C30 alkyl or C8 to C30 alkenyl; $R^{X2}$ is C1 to C29 alkyl or C2 to C29 alkenyl; and the number of carbon atoms of the alkyl or alkenyl of $R^{X2}$ is smaller than the number of carbon atoms of the alkyl or alkenyl of $R^{X1}$.
(7) The method according to any one of (4) to (6), wherein the cleavage reagent and the deprotecting agent contain butylamine and/or benzylamine.

(8) The method according to any one of (4) to (7), comprising a step of washing the compound (V) with an organic solvent.
(9) A method for producing a double-stranded oligonucleotide, comprising steps of:
obtaining the compound (VII) or (X) by the method according to any one of (4) to (8), and
annealing an oligonucleotide comprising a sequence capable of hybridizing to an oligonucleotide of the compound (VII) or (X) to form a double strand.
(10) The method according to (9), wherein the double-stranded oligonucleotide is a double-stranded oligonucleotide composed of a chain of a formula:

[Formula 18]

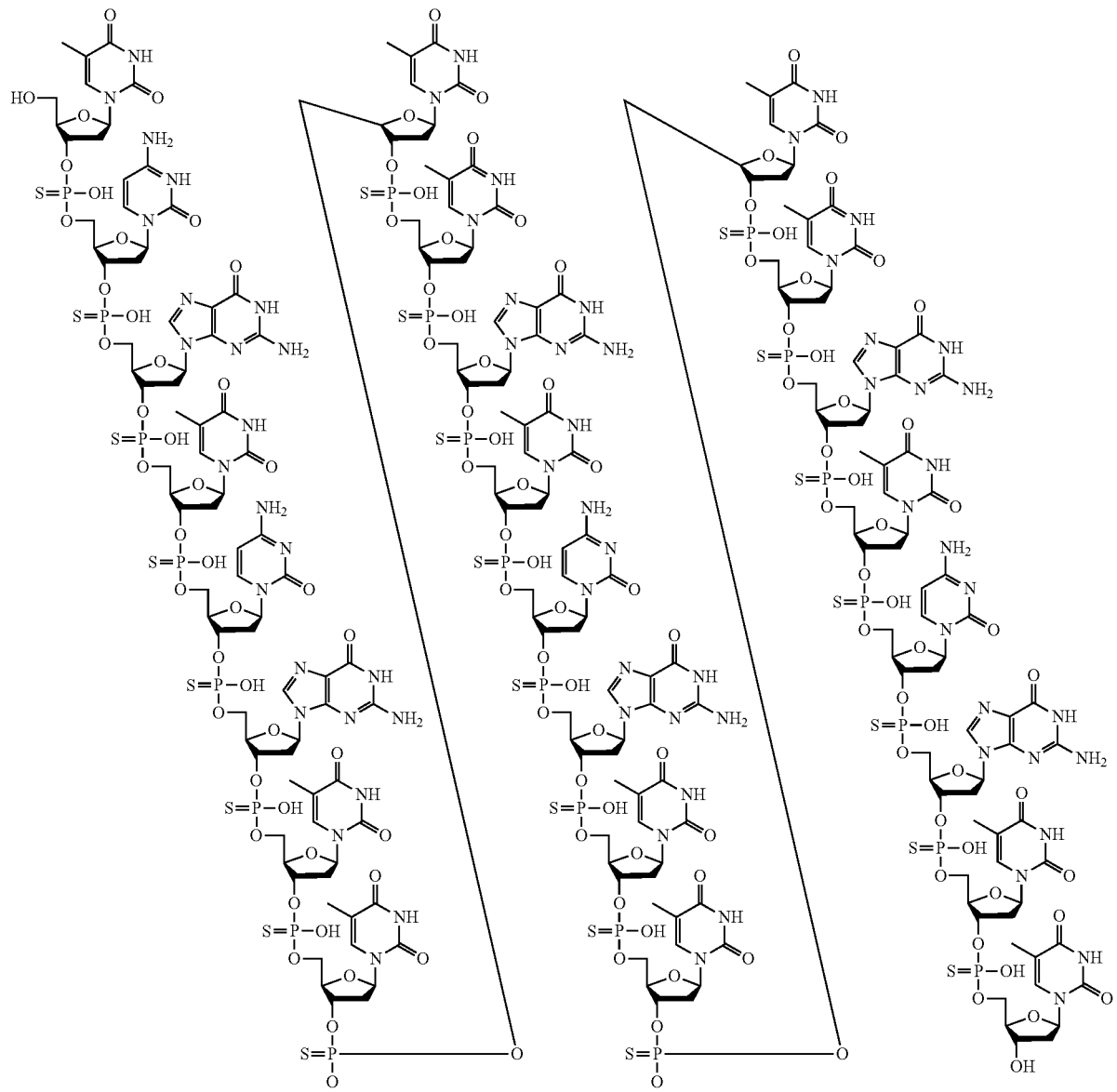

(ODN2006)

(an oligonucleotide consisting of the bases described in SEQ ID NO: 1) and a chain of a formula selected from the following:
a formula:
[Formula 19]
(S-1)
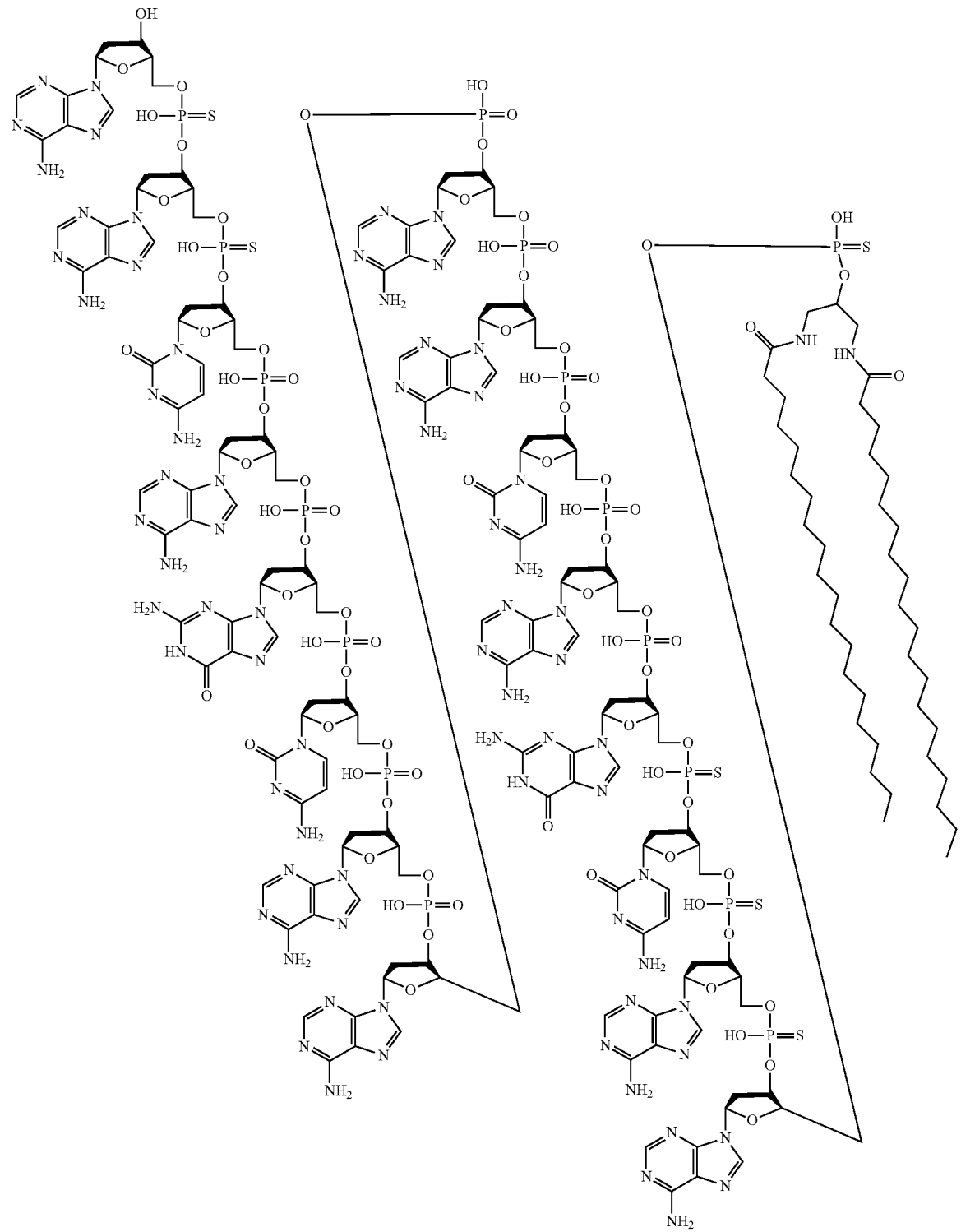

(an oligonucleotide consisting of the bases described in SEQ ID NO: 2 and comprising a bifurcated lipid at the 5' end)
a formula:
[Formula 20]
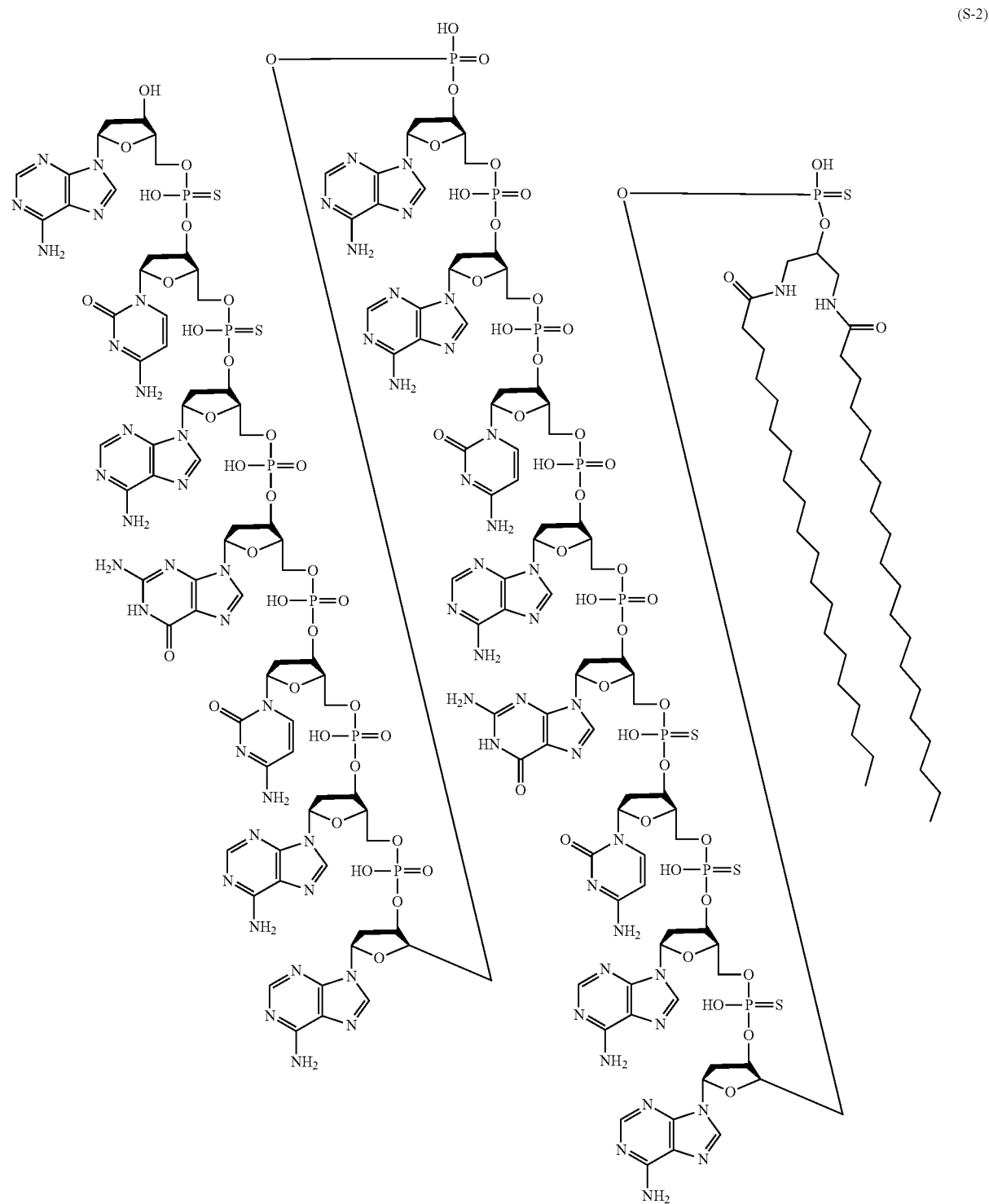
(S-2)

(an oligonucleotide consisting of the bases described in SEQ ID NO: 3 and comprising a bifurcated lipid at the 5' end)
a formula:
[Formula 21]
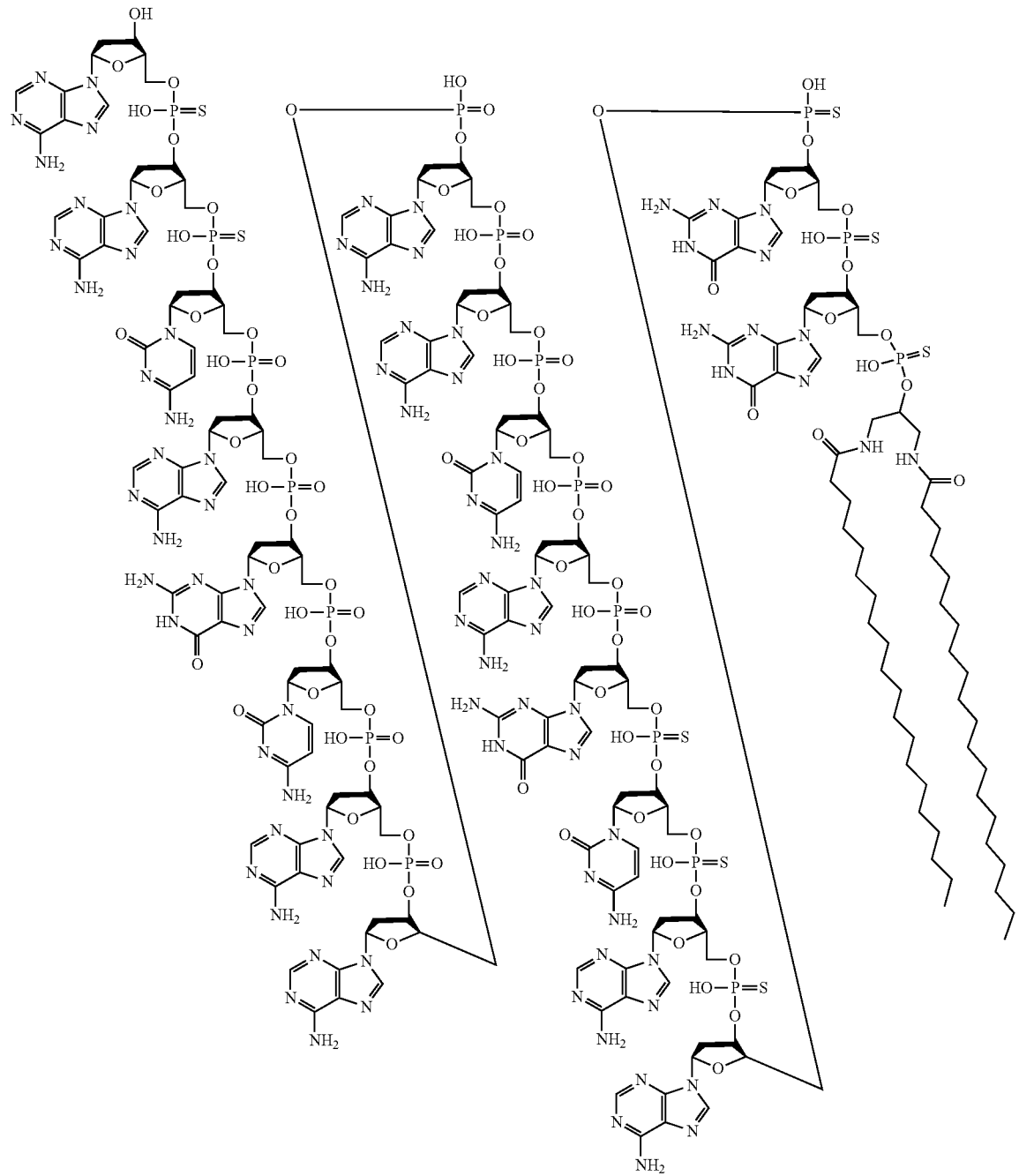
(S-3)

(an oligonucleotide consisting of the bases described in SEQ ID NO: 4 and comprising a bifurcated lipid at the 5' end)
a formula:
[Formula 22]
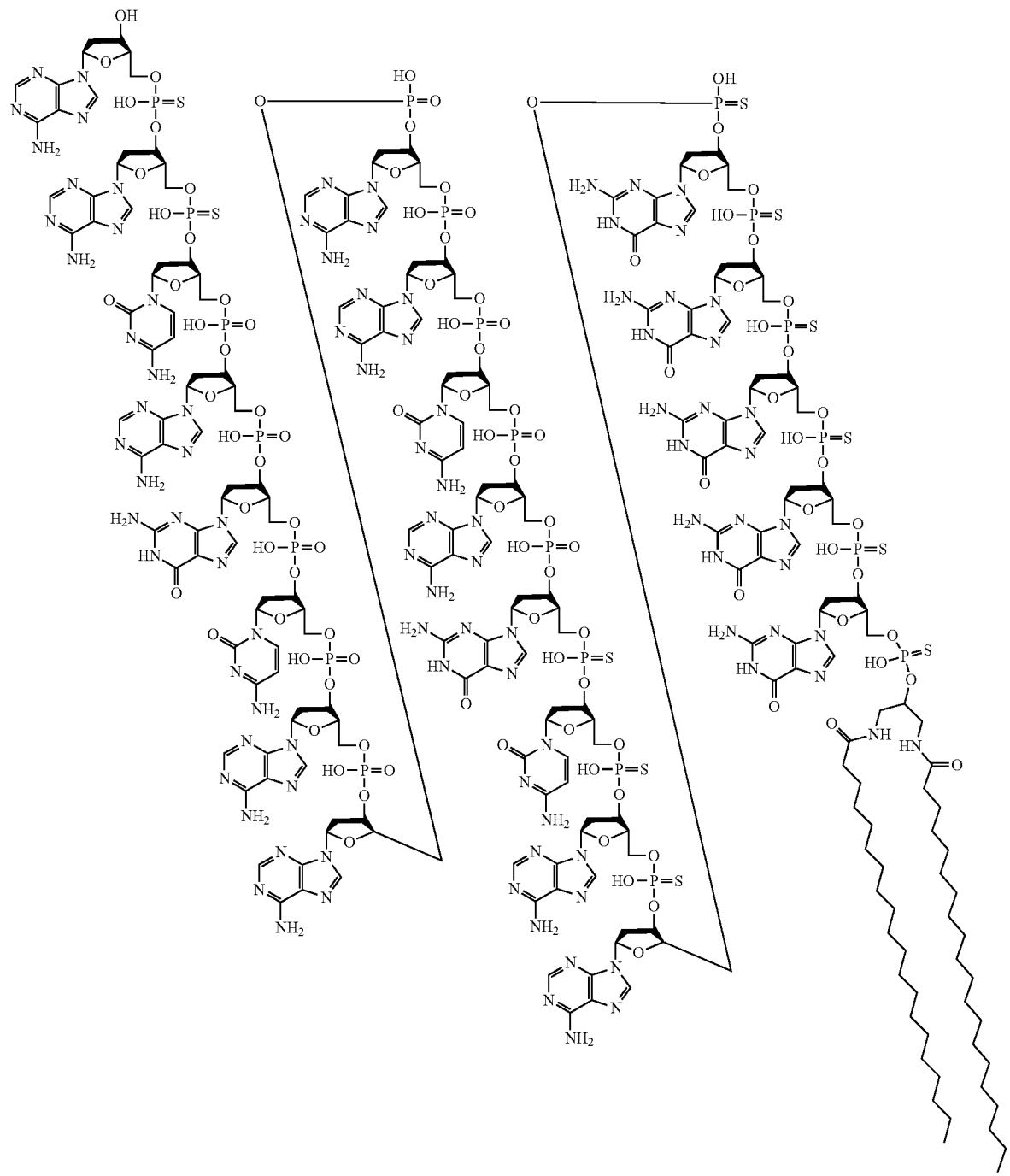
(S-4)

(an oligonucleotide consisting of the bases described in SEQ ID NO: 5 and comprising a bifurcated lipid at the 5' end)
a formula:
[Formula 23]
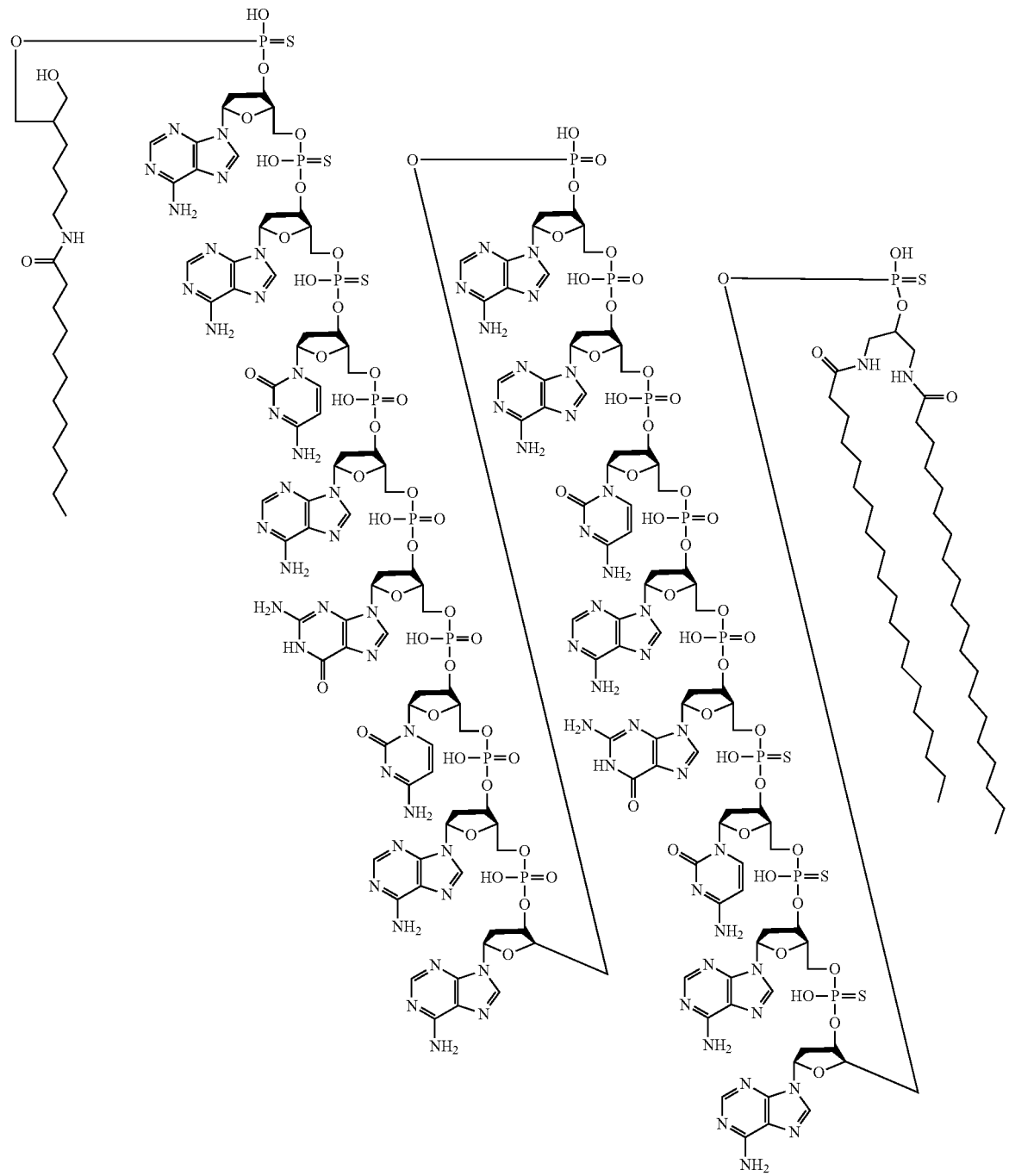
(S-5)

(an oligonucleotide consisting of the bases described in SEQ ID NO: 2 and comprising a bifurcated lipid at the 5' end)
and a formula:
[Formula 24]
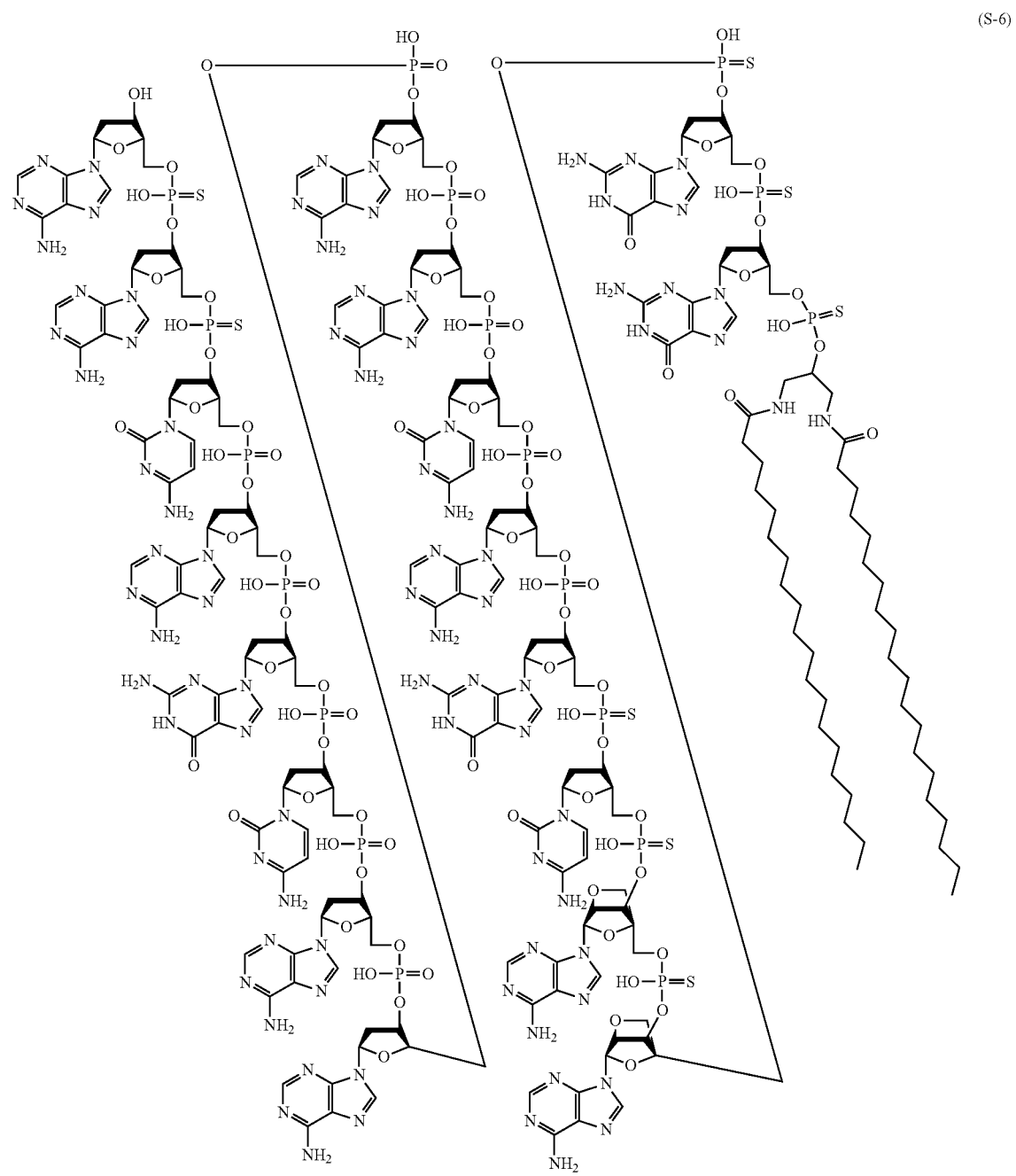
(an oligonucleotide consisting of the bases described in SEQ ID NO: 4 and comprising a bifurcated lipid at the 5' end).
(11) The method according to any one of (4) to (10), wherein the compound of formula (II) is the compound according to (1).

(12) The method according to (11), wherein the compound of formula (II) is the compound according to (2).

(13) The method according to (11), wherein the compound of formula (II) is the compound according to (3).

(14) A compound of formula (IV):

[Formula 25]

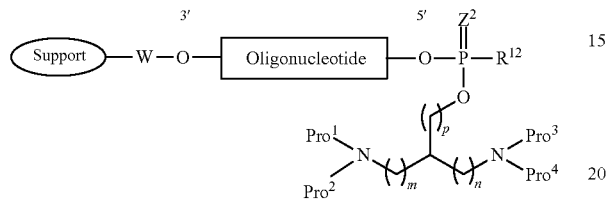

(IV)

wherein each symbol has the same meaning as described above.

(15) A compound of formula (XI):

[Formula 26]

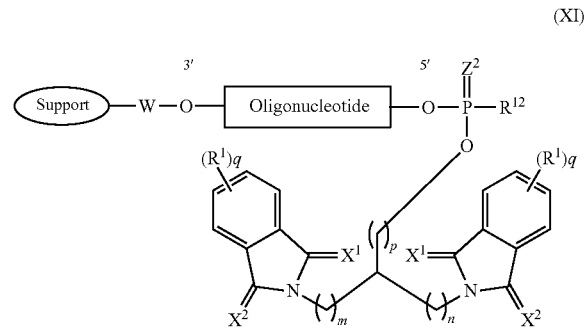

(XI)

wherein each symbol has the same meaning as described above.

(16) A compound of formula (V):

[Formula 27]

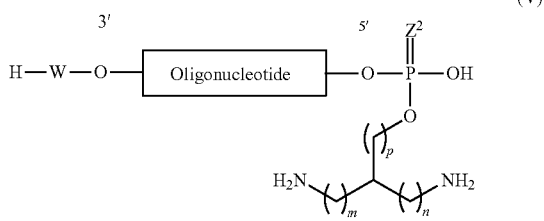

(V)

wherein each symbol has the same meaning as described above.

(17) A compound of formula (VIII):

[Formula 28]

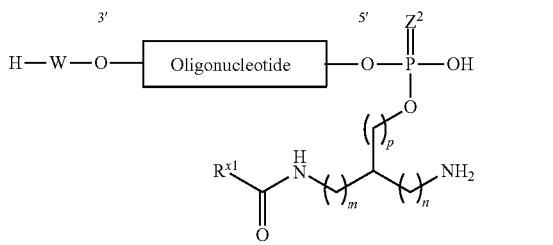

(VIII)

wherein each symbol has the same meaning as described above.

Effect of the Invention

A method for producing a bifurcated lipid-linked oligonucleotide of the present invention using an amidite of the present invention in which two hydrogen atoms linked to a nitrogen atom to which an acyl lipid is to be introduced are substituted with protecting groups and conditions thereof are useful for suppressing generation of byproducts and reliably obtaining a target final product. That is, the production method of the present invention is very useful when synthesizing a product requiring high quality such as a pharmaceutical product.

In particular, an intermediate which is a compound of formula (I) or its salt is a crystal, and quality control (analysis of purity, control and management of amount of impurities, etc.) is possible. The intermediate can be used to efficiently synthesize a bifurcated lipid-linked oligonucleotide.

MODE FOR CARRYING OUT THE INVENTION

Terms used herein are used in the meaning that is commonly used in the field unless otherwise specified.

In the present invention, gene manipulation methods known in the field can be used. Examples thereof include methods described in Molecular Cloning, A Laboratory Manual, Forth Edition, Cold Spring Harbor Laboratory Press (2012), Current Protocols Essential Laboratory Techniques, Current Protocols (2012), and the like.

Each term used herein will be described below. In the present specification, each term has the same meaning when used alone or together with other terms.

The term "halogen" includes a fluorine atom, a chlorine atom, a bromine atom, and an iodine atom. In particular, a fluorine atom and a chlorine atom are preferable.

The term "alkyl" includes a C1 to C15, preferably a C1 to C10, more preferably a C1 to C6, and further preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

A preferred embodiment of "alkyl" includes methyl, ethyl, n-propyl, isopropyl, n-butyl, isobutyl, sec-butyl, tert-butyl or n-pentyl.

The term "alkyl" in $R^{X1}$ in formula (VI) and $R^{X2}$ in formula (IX) includes a C1 to C50, a C1 to C40, a C1 to C30, more preferably a C8 to C30, and further preferably a C12 to C30 linear or branched hydrocarbon group.

The term "alkenyl" includes a C2 to C15, preferably a C2 to C10, more preferably a C2 to C6, and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl, and the like.

A preferred embodiment of "alkenyl" includes vinyl, allyl, propenyl, isopropenyl, or butenyl.

The term "alkenyl" in $R^{X1}$ in formula (VI) and $R^{X2}$ in formula (IX) includes a C2 to C50, a C2 to C40, a C2 to C30, more preferably a C8 to C30, and further preferably a C12 to C30 linear or branched hydrocarbon group having one or more double bond(s) at any position(s).

The term "alkynyl" includes a C2 to C10, preferably a C2 to C8, more preferably a C2 to C6, and further preferably a C2 to C4 linear or branched hydrocarbon group having one or more triple bond(s) at any position(s). Furthermore, it may have double bond(s) at any position(s). For example, it includes ethynyl, propynyl, butynyl, pentynyl, hexynyl, heptynyl, octynyl, nonynyl, decynyl, and the like.

A preferred embodiment of "alkynyl" includes ethynyl, propynyl, butynyl, or pentynyl.

The term "aromatic carbocyclyl" means a cyclic aromatic hydrocarbon group which is monocyclic or polycyclic having two or more rings. Examples include phenyl, naphthyl, anthryl, phenanthryl, and the like.

A preferred embodiment of "aromatic carbocyclyl" includes phenyl.

Substituents for "substituted alkyl", "substituted alkenyl" and "substituted alkynyl" include following substituents. A carbon atom(s) at any position(s) may be bonded to one or more group(s) selected from the following substituents.

Substituents: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

Examples of the substituent on rings of "substituted aromatic carbocyclyl", "substituted non-aromatic carbocyclyl", "substituted aromatic heterocyclyl", and "substituted non-aromatic heterocyclyl" include the following substituents. An atom(s) at any position(s) on the ring may be bonded to one or more group(s) selected from the following substituents.

Substituents: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, mono alkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

Examples of the method for producing a bifurcated lipid-linked oligonucleotide of the present invention include the methods described in the above (4) to (13).

The production method of the present invention described in the above (4) is shown below.

[Formula 29]

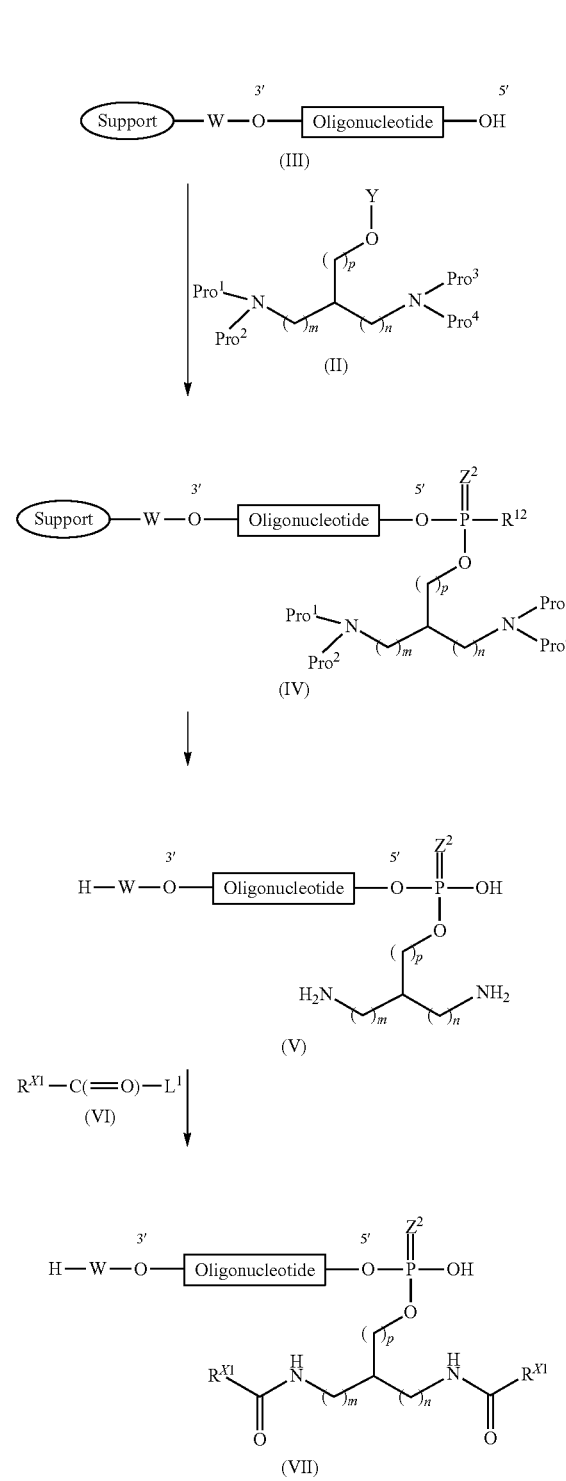

wherein each symbol has the same meaning as described above.

With regard to the production method of the present invention described in the above (5), steps that follow the compound of formula (V) are shown below. Steps up to obtain the compound of formula (V) are the same as those in the above (4).

[Formula 30]

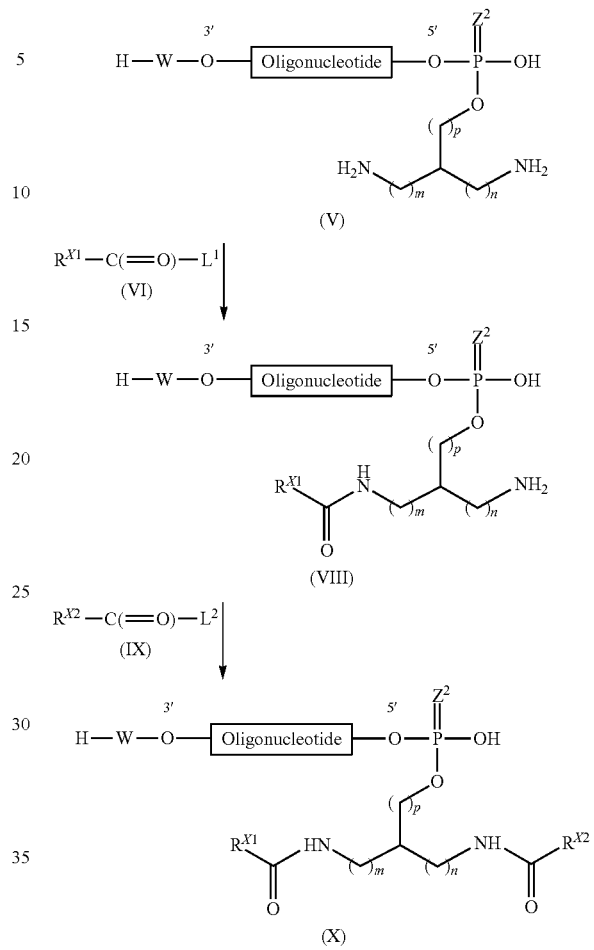

wherein each symbol has the same meaning as described above.

1. Synthesis of Oligonucleotide

A compound of formula (II) or its salt is reacted with an oligonucleotide of formula (III) to obtain a compound of formula (IV). As a synthesis method, a solid phase synthesis method using phosphoramidite can be used. For example, it is disclosed in the following Examples, Tetrahedron Letters 22, 1859-1862 (1981), and the like. Specifically, the compound of formula (IV) can be easily synthesized by first synthesizing the compound of formula (III) with a commercially available automated nucleic acid synthesizer (for example, a synthesizer manufactured by GE Healthcare (Cytiva), Applied Biosystems or Dainippon Seiki Co., Ltd.), and introducing the compound of formula (II) or its salt in a final cycle.

The term "solid phase carrier" is a solid support that is used for solid phase synthesis of an oligonucleotide, can carry an oligonucleotide, and is insoluble in a reaction solvent. Commercially available products generally used in the field can be used as a solid phase carrier in the production method of the present invention, and appropriate modifications can also be added to functional groups present on carrier surfaces of these commercially available products as necessary.

The compound of formula (II) or its salt can be produced by introducing each protecting group ($Pro^1$, $Pro^2$, $Pro^3$, and $Pro^4$) into compound (a) described in the present specification.

The term "oligonucleotide" means a nucleotide in which a plurality of identical or different nucleosides are linked together.

Sequence and modification of "oligonucleotide" in the present invention are not particularly limited. DNA, RNA or a nucleic acid comprising a nucleotide having a modification(s) known in the field for a nucleobase, sugar or internucleoside linkage or the like can be used. Also, chain length of the oligonucleotide is not particularly limited, and is, for example, 8 to 50 bases, 8 to 40 bases, 8 to 30 bases, 10 to 25 bases, or 15 to 25 bases.

In the present specification, O linked to left of "Oligonucleotide" in formulae (III) to (V), (VII), (VIII), (X), and (XI) means an oxygen atom at 3' end of an oligonucleotide sequence, and O linked to right means an oxygen atom at 5' end of the oligonucleotide sequence.

The "Oligonucleotide" is not particularly limited as long as it is an oligonucleotide that needs to bind a bifurcated lipid. Examples thereof include a CpG oligonucleotide described in Patent Document 1, "an oligonucleotide containing a sequence capable of hybridizing to a CpG oligonucleotide" described in Patent Documents 2 and 3, and "an oligonucleotide having expression suppressing activity of target gene (a single strand among double-stranded oligonucleotides such as siRNA and miRNA, antisense oligonucleotide, and the like)" described in Patent Document 4. By binding the bifurcated lipid, it is possible to improve pharmaceutical activity (immunostimulatory activity in the case of adjuvant, activity of suppressing expression of target gene in the case of nucleic acid drug, and the like) of the oligonucleotide to which the lipid is linked or the oligonucleotide comprising a sequence capable of hybridizing with the oligonucleotide.

In the present specification, an amino moiety in adenine, guanine or cytosine and a hydroxy moiety in phosphoric acid in "Oligonucleotide" in formulae (III), (IV) and (XI) are protected with a protecting group in order to prevent side reactions. As the protecting group, a protecting group commonly used in the field can be used. Examples of the amino protecting group include pivaloyl, pivaloyloxymethyl, trifluoroacetyl, phenoxyacetyl, 4-isopropylphenoxyacetyl, 4-tert-butylphenoxyacetyl, acetyl, benzoyl, isobutyryl, dimethylaminomethylene 9-fluorenylmethyloxycarbonyl, and the like. The amino protecting group is preferably phenoxyacetyl, 4-isopropylphenoxyacetyl, acetyl, benzoyl, isobutyryl, or a dimethylformamidinyl group. The protecting group for the amino moiety of adenine is particularly preferably a benzoyl group. The protecting group for the amino moiety of guanine is particularly preferably a dimethylaminomethylene group or an isobutyryl group. The protecting group for the amino moiety of cytosine is preferably a benzoyl group or an acetyl group, and particularly preferably an acetyl group. Examples of the protecting group for hydroxy group of phosphoric acid include 2-cyanoethyl and the like.

The "protecting group" for $Pro^1$, $Pro^2$, $Pro^3$, and $Pro^4$ is not particularly limited as long as it can stably protect amino during nucleic acid synthesis. Specifically, it refers to a protecting group that is stable under acidic or neutral conditions and can be cleaved by a chemical method such as hydrogenolysis, hydrolysis, electrolysis and photolysis, and examples thereof include formyl, substituted or unsubstituted alkylcarbonyl, substituted or unsubstituted aromatic carbocyclylcarbonyl, substituted or unsubstituted alkoxycarbonyl, substituted or unsubstituted alkenyloxycarbonyl, and the like.

The phrase "$Pro^1$, $Pro^2$, $Pro^3$ and $Pro^4$ are taken together to form a protecting group" means that $Pro^1$, $Pro^2$, $Pro^3$ and $Pro^4$ are taken together to form a protecting group containing a nitrogen-containing ring. The protecting group is not particularly limited, and examples thereof include a group of

[Formula 31]

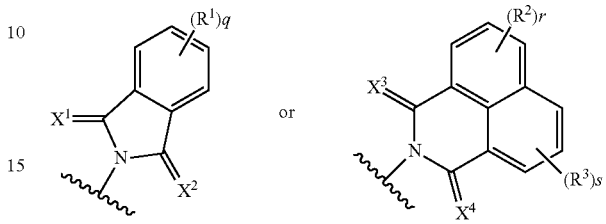

wherein each symbol has the same meaning as described above.

As the compound of formula (II), the following embodiments are preferable.

m is preferably 0 to 2 among integers of 0 to 5, and particularly preferably 1.

n is preferably 1 or 2 among integers of 0 to 5, and particularly preferably 1.

p is preferably 0 or 1 among integers of 0 to 5, and particularly preferably 0.

Examples of Y include a group of formula (Y-1), a group of formula (Y-2), and a group of formula (Y-3).

$R^4$ is preferably alkyl or cyanoalkyl. $R^5$ is preferably alkyl.

Examples of formula (Y-1) include a group of formula: —$P(OC_2H_4CN)(N(i-Pr)_2)$, wherein i-Pr means isopropyl.

$R^6$ is preferably O, and $R^7$ is preferably a hydrogen atom.

Examples of formula (Y-2) include a group of formula: —$P(=O)(OH)_2$.

$R^8$ is preferably O, and $R^9$ is preferably a hydrogen atom.

Examples of formula (Y-3) include a group of formula: —$P(=O)H(OH)$.

The compound of formula (II) is particularly preferably a compound of formula (I) and its salt. More preferred examples thereof include the compound described in the above (2) or (3) or its salt.

As the compound of formula (I), the following embodiments are preferable.

It is preferred that A and B are each independently

[Formula 32]

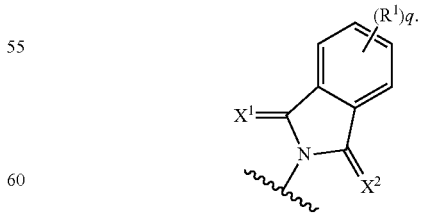

$X^1$, $X^2$, $X^3$, and $X^4$ are preferably O.

Y is preferably a group of formula (Y-1).

The compound of formula (I) is particularly preferably a compound of the following formula or its salt.

[Formula 33]

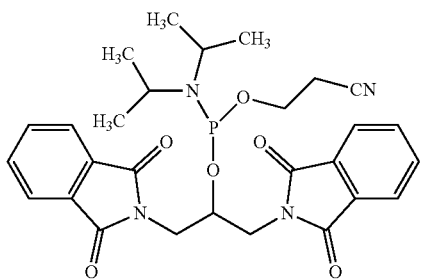

One or more hydrogen, carbon or other atoms of the compound of formula (I) or (II) of the present invention may be substituted with isotopes of hydrogen, carbon or other atoms.

For example, the compound of formula (I) or (II) includes all radiolabeled forms of the compound of formula (I) or (II). Such "radiolabeling", "radiolabeled form" and the like of the compound of formula (I) or (II) are each encompassed by the present invention and are useful as research and/or diagnostic tools in metabolic pharmacokinetic studies and binding assays. Examples of the isotopes that can be incorporated into the compound of formula (I) or (II) of the present invention include hydrogen, carbon, nitrogen, oxygen, phosphorus, sulfur, fluorine, and chlorine, like 2H, 3H, 13C, 14C, 15N, 18O, 17O, 31P, 32P, 35S, 18F, and 36Cl, respectively. The radiolabeled compound of the present invention can be prepared by methods well known in the art. For example, a tritium-labeled compound of formula (I) or (II) can be prepared by introducing a tritium to a certain compound of formula (I) or (II), for example, through a catalytic dehalogenation reaction using a tritium. This method may include reacting a suitably halogen-substituted precursor of the compound of formula (I) or (II) with tritium gas in the presence of a suitable catalyst such as Pd/C, in the presence or absence of a base. The other appropriate method of preparing a tritium-labeled compound can be referred to document "Isotopes in the Physical and Biomedical Sciences, Vol. 1, Labeled Compounds (Part A), Chapter 6 (1987)". A 14C-labeled compound can be prepared by using a raw material having 14 C.

Examples of the salt of the compound of formula (I) or (II) include the following salts.

Examples of basic salts include alkali metal salts such as sodium salts and potassium salts; alkaline earth metal salts such as calcium salts and magnesium salts; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts, and ethylenediamine salts; aralkylamine salts such as N,N-dibenzylethylenediamine and benethamine salts; heterocyclic aromatic amine salts such as pyridine salts, picoline salts, quinoline salts, and isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts, and tetrabutylammonium salts; basic amino acid salts such as arginine salts and lysine salts; and the like.

Examples of acid salts include inorganic acid salts such as hydrochlorides, sulfates, nitrates, phosphates, carbonates, hydrogen carbonates, and perchlorates; organic acid salts such as benzoates, acetates, propionates, lactates, maleates, fumarates, tartrates, malates, citrates, and ascorbates; sulfonates such as methanesulfonates, isethionates, benzenesulfonates, and p-toluenesulfonates; acidic amino acid salts such as aspartates and glutamates; and the like. Acid addition salts herein includes the acid salts.

The compound of formula (I) or (II) or its salt may form a solvate and/or a crystal polymorph, and the compound of formula (I) or (II) also includes such solvates and crystal polymorphs of various types. A solvate means a solvate of the compound of formula (I) or (II) or its salt, and examples thereof include solvate of which solvent is alcohol (e.g., ethanol), hydrate, toluene, and the like Examples of the hydrate include monohydrate, dihydrate, and the like. The "solvate" may be one in which any number of solvent molecules (e.g., water molecules or the like) is coordinated with the compound of formula (I) or (II). When the compound of formula (I) or (II) or its salt is allowed to stand in the atmosphere, the compound may absorb water, resulting in attachment of adsorbed water or formation of hydrate. In addition, the compound of formula (I) or (II) or its salt may be recrystallized to form a crystal polymorph thereof.

A general production method of the compound of formula (I) of the present invention is exemplified below. In extraction, purification, and other operations, any process commonly performed therefor in organic chemistry experiments can be employed.

An example of the production method when A and B are the same in the compound of formula (I) is shown below.

[Formula 34]

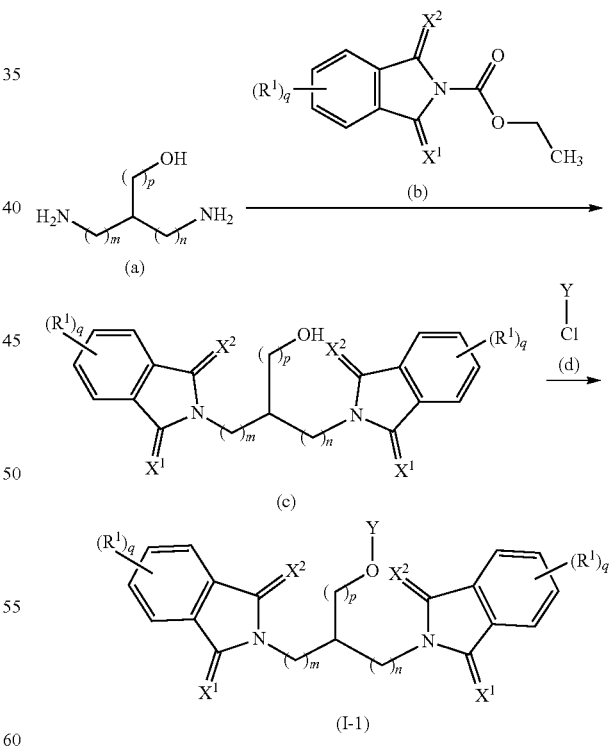

wherein each symbol has the same meaning as in formula (I).

Step 1-1

Acetonitrile is added to compound (b), and the mixture is stirred. After adding triethylamine, a solution obtained by dissolving compound (a) in acetonitrile and acetonitrile are added thereto. The mixture is stirred vigorously, and a solid is filtered. The obtained solid is washed with acetonitrile and then dried to obtain compound (c).

Step 2-1

The compound (c) obtained in Step 1-1 and N-methylpyrrolidone are added to N-methylpyrrolidone, and the mixture is stirred. After adding N,N-diisopropylethylamine, compound (d) and N-methylpyrrolidone are added thereto. The mixture is stirred at room temperature, tap water is added thereto, and the mixture is further stirred. After adding tap water thereto, the mixture is further stirred. Thereafter, tap water is further added thereto and stirred, and a solid is filtered. The obtained solid is washed with 2-propanol and then dried to obtain compound (I-1).

An example of the production method when A and B are different in the compound of formula (I) is shown below.

wherein $R^{1-1}$ and $R^{1-2}$ have the same meaning as $R^1$ in formula (I), $X^{1-1}$ and $X^{1-2}$ have the same meaning as $X^1$ in formula (I), $X^{2-1}$ and $X^{2-2}$ have the same meaning as $X^2$ in formula (I), q-1 and q-2 have the same meaning as q in formula (I), and other symbols have the same meaning as those in formula (I).

Step 1-2

In Step 1-1, the amount of the compound (b) to be added is reduced to obtain compound (e). Next, compound (f) is added to the compound (e) to obtain compound (g).

Step 2-2

Compound (I-2) is obtained in the same manner as Step 2-1 by using the obtained compound (g).

In place of the compounds (b) and (f), a compound of a formula:

[Formula 35]

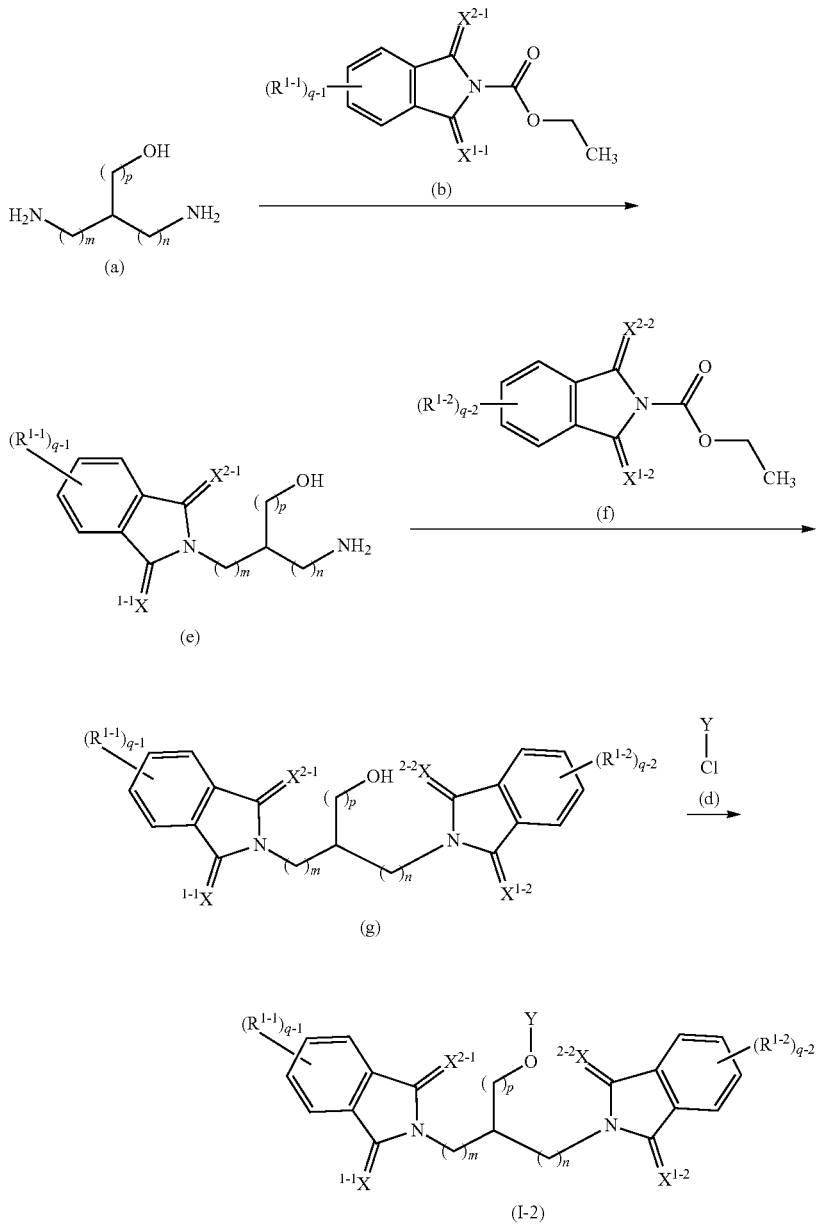

[Formula 36]

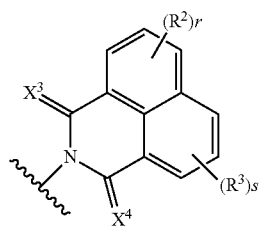

can be used.

2. Cutting Out From Resin, Deprotection of Base and Phosphoric Acid

In the presence of a cleavage reagent and a deprotecting agent, protecting groups in a compound of formula (IV) (including a protecting group(s) of a base(s) and phosphoric acid(s) in an oligonucleotide) is deprotected and cut out from a solid phase carrier to obtain a compound of formula (V).

The steps of deprotection and cutting out from a solid phase carrier can also be carried out simultaneously, and can be carried out using the same reagent or using two or more reagents. It can also be carried out at different temperatures and using different reagents.

As "a cleavage reagent and a deprotecting agent", a reagent usually used in the field can be used as long as it is a reagent having an action of cutting out an oligonucleotide from a solid phase carrier and/or deprotecting a protecting group. Examples thereof include ammonia, amines, and the like. The cleavage reagent and the deprotecting agent preferably contain butylamine and/or benzylamine. The cleavage reagent and the deprotecting agent particularly preferably contain n-butylamine or benzylamine. Furthermore, when cytosine is present in a sequence of the oligonucleotide, it is preferable to synthesize the oligonucleotide using amidite in which an amino group of cytosine is protected with an acetyl group, and then use a cleavage reagent and a deprotecting agent containing n-butylamine or benzylamine.

Note that a protecting group in $R^{12}$ in the compound of formula (IV) can be first removed using diethylamine, and then the other protecting groups in the compound of formula (IV) can be deprotected and cut out from the solid phase carrier.

3. Introduction of Lipids (Acylation Reaction)

A compound of formula (VI) is reacted with a compound of formula (V) to obtain a compound of formula (VII).

In addition, a compound of formula (VI) is reacted with a compound of formula (V) to obtain a compound of formula (VIII), and a compound of formula (IX) is reacted with the compound of formula (VIII) to obtain a compound of formula (X).

In the step of introduction of lipids, it is preferable to wash the compound (V) with an organic solvent before reacting the compound of formula (V) with the compound of formula (VI).

Examples of the "organic solvent" include hexane, heptane, diethyl ether, diisopropyl ether, methyl tert-butyl ether, cyclopropyl methyl ether, tetrahydrofuran, 2-methyltetrahydrofuran, anisole, toluene, methyl isobutyl ketone, methyl ethyl ketone, ethyl acetate, isopropyl acetate, n-butyl acetate, n-butanol, dichloromethane, chloroform, and the like. Particularly preferred is methyl tert-butyl ether.

$R^{X1}$ is alkyl or alkenyl, and is preferably C8 to C30 alkyl or C8 to C30 alkenyl.

$R^{X2}$ is alkyl or alkenyl, and is preferably C1 to C29 alkyl or C2 to 29 alkenyl. Furthermore, a carbon number of the alkyl or alkenyl of $R^{X2}$ is preferably smaller than a carbon number of the alkyl or alkenyl of $R^{X1}$.

The "leaving group" of $L^1$ and $L^2$ is not particularly limited as long as it is a substituent that leaves upon condensation of a carboxylic acid and an amine. Examples thereof include halogen, substituted or unsubstituted alkylimino, substituted or unsubstituted alkylcarbonyloxy, substituted or unsubstituted alkylsulfonyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted aromatic carbocyclylsulfonyloxy, substituted or unsubstituted aromatic carbocyclylalkylsulfonyloxy, and the like. Preferred are halogen, acetyloxy, benzoyloxy, methanesulfonyloxy, trifluoromethanesulfonyloxy, p-toluenesulfonyloxy, o-nitrobenzenesulfonyloxy, N,N'-dicyclohexylcarbamimidoyloxy, N,N'-diisopropylcarbamimidoyloxy, (N-(3-(dimethylamino) propyl)-N'-ethylcarbamimidoyloxy, N-succinimidyloxy, and the like. Particularly preferred is N-succinimidyloxy.

In this step, a condensing agent can be used. As the condensing agent, an amide condensing agent used for condensation of a carboxyl group and an amino group can be used. Examples thereof include carbodiimides (for example, N,N'-dicyclohexylcarbodiimide, N,N'-diisopropylcarbodiimide, 1-ethyl-3-(3-dimethylaminopropyl) carbodiimide hydrochloride, diphenylphosphate azide, BOP reagents (for example, BOP, PyBop, TBTU, etc.), HBTU, DMT-MM, 1,1'-carbonylbis-1H-imidazole, 2-chloro 1,3-dimethylimidazolium chloride, 4-(4,6-dimethoxy-1,3,5-triazine-2-yl)-4-methylmorpholinium chloride, N-hydroxysuccinimide, sodium N-hydroxysuccinimide, and the like). Preferred are N,N'-dicyclohexylcarbodiimide, N,N'-diisopropylcarbodiimide, 1-ethyl-3-(3-dimethylaminopropyl) carbodiimide hydrochloride, N-hydroxysuccinimide, sodium N-hydroxysuccinimide, and the like. Particularly preferred is N-hydroxysuccinimide or N,N'-dicyclohexylcarbodiimide.

When $L^1$ or $L^2$ is OH, it is preferable to use a condensing agent.

The bifurcated lipid-linked oligonucleotide (single strand) obtained using the production method of the present invention can be used as, for example, a nucleic acid drug such as antisense.

4. Preparation of Double-Stranded Oligonucleotide

A double-stranded oligonucleotide is obtained by annealing an oligonucleotide containing a sequence hybridizable to an oligonucleotide of the compound (VII) or (X) obtained using the production methods of A to C.

The oligonucleotide to be annealed may be shorter by one or several bases as long as it hybridizes with the oligonucleotide in the compound (VII) or (X). In addition, the oligonucleotide may be longer than the oligonucleotide in the compound (VII) or (X), by adding one or several bases to one side or both sides of a hybridizing site.

The phrase "one or several bases" means 1 to 10, 1 to 5, 1 to 3, or 1 or 2 bases.

Preferred length of the oligonucleotide to be annealed depends on length of the oligonucleotide in the compound (VII) or (X). For example, the preferred length is a length of 50% or more, a length of 60% or more, a length of 70% or more, a length of 50 to 100%, a length of 60 to 100%, and a length of 70 to 100% with respect to length of chain of the oligonucleotide in the compound (VII) or (X). The length is particularly preferably a length of 50 to 100% with respect to length of chain of the oligonucleotide in the compound (VII) or (X).

The oligonucleotide to be annealed also includes those in which one or several mismatches exist at the hybridizing site as long as they can hybridize with the oligonucleotide in the compound (VII) or (X) under stringent conditions. Examples thereof include oligonucleotides in which the hybridizing site has at least 70% or more, preferably 80% or more, more preferably 90% or more, and most preferably 95% or more homology with a target sequence.

Here, the homology shows similarity as a score, for example, by using BLAST, a search program using an algorithm developed by Altschul et al. (The Journal of Molecular Biology, 215, 403-410 (1990).).

The phrase "stringent conditions" means conditions under which a certain base sequence forms a hybrid with a specific sequence (so-called specific hybrid), and a base sequence having no equivalent function does not form a hybrid with the specific sequence (so-called non-specific hybrid). Those skilled in the art can easily select such conditions by changing temperature during hybridization reaction and washing, salt concentrations of a hybridization reaction solution and a washing solution, and the like. Specifically, an example of a stringent condition of the present invention is, but not limited to a condition of hybridizing at 42° C. in 6×SSC (0.9 M NaCl, 0.09 M trisodium citrate) or 6×SSPE (3 M NaCl, 0.2 M $NaH_2PO_4$, 20 mM EDTA·2Na, pH 7.4) and further washing by 0.5×SSC at 42° C. As a hybridization method, a method commonly known in the field, for example, a Southern blot hybridization method or the like can be used. Specifically, it can be performed according to a method described in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press), or the like.

The phrase "one or several mismatches" means 1 to 5, preferably 1 to 3, and further preferably 1 or 2 mismatches.

The bifurcated lipid-linked oligonucleotide (double strand) obtained using the production method of the present invention can be used as the method for producing a bifurcated lipid-linked oligonucleotide described in Patent Documents 2 to 4, for example, as in the above (10).

Unless otherwise stated, numerical values in the description and claims are approximate values. Variation of numerical values is due to device calibration, device error, material purity, crystal size, sample size, and other factors.

Various substituents of the compound of the present invention can be introduced with reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS, and the like.

EXAMPLES

Hereinafter, the present invention will be described in more detail with reference to Examples of the present invention, but the present invention is not limited thereto.

NMR analysis of the compounds obtained in Examples was performed with a 400 MHz superconducting nuclear magnetic resonance apparatus, and measurement was performed using $CDCl_3$.

Example 1 Synthesis of Bifurcated Lipid-Linked Oligonucleotides Using Intermediate (Amidite) of Present Invention 1) Synthesis of Amidite

[Formula 37]

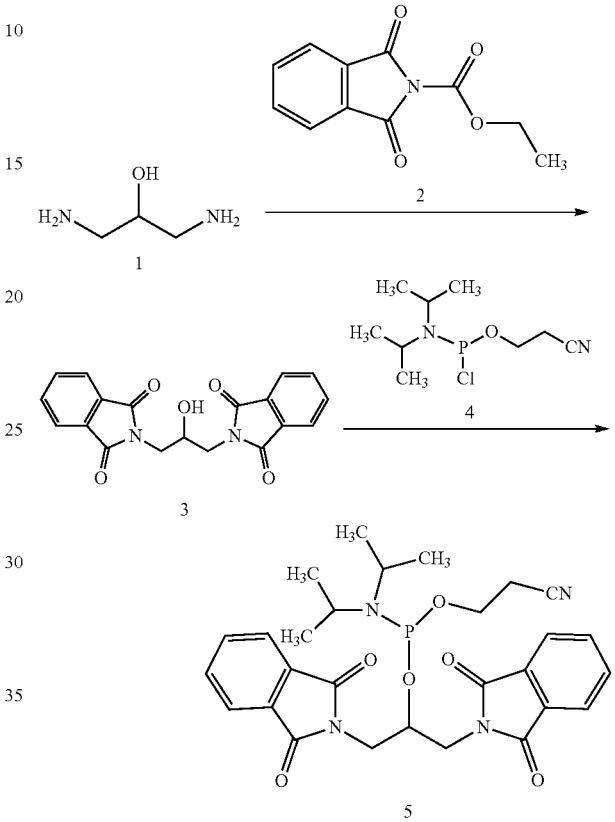

Step 1

Acetonitrile (600 mL) was added to compound 2 (133.76 g, 610.22 mmol), and the mixture was stirred. After adding triethylamine (30.87 g, 305.07 mmol), a solution obtained by dissolving compound 1 (25.00 g, 277.38 mmol) in acetonitrile (125 mL) and acetonitrile (25 mL) were added thereto. The mixture was stirred vigorously at room temperature for 2.5 hours, and a solid was filtered. The obtained solid was washed with acetonitrile (300 mL) and then dried to obtain compound 3 (72.73 g, 207.6 mmol) as a white solid.

The following conditions were used for UPLC analysis.

Mobile phase [A]: 60 mM ammonia-ammonium acetate-containing buffer solution (pH 8.0), Mobile phase [B]: acetonitrile Gradient: linear gradient of 15% to 50% solvent FBI was performed in 12 minutes, and then linear gradient of 50% to 95% solvent FBI was performed in 3 minutes, and 95% solvent FBI was kept for 1 minute.

Column: ACQUITY UPLC (registered trademark) BEH Phenyl (1.7 μm, i.d. 2.1×100 mm) (Waters)

Flow rate: 0.3 mL/min

UV Detection wavelength: 295 nm $^1$H NMR ($CDCl_3$) δ:7.85-7.90 (m, 4H), 7.72-7.76 (m, 4H), 4.28-4.34 (m, 1H), 3.83-3.93 (m, 4H), 3.12 (d, 1H, J=6.3 Hz).

$^{13}$C-NMR (CDCl$_3$) δ: 42.21, 68.75, 123.53, 131.94, 134.19, 168.68.

ESI-MS (m/z): 351 (M+1), 373 (M+23).

Step 2

Compound 3 (20.00 g, 57.09 mmol) and N-methylpyrrolidone (10 mL) were added to N-methylpyrrolidone (220 mL), and the mixture was stirred. After adding N,N-diisopropylethylamine (20.68 g, 160.01 mmol), compound 4 (21.62 g, 91.35 mmol) and N-methylpyrrolidone (10 mL) were added thereto. The mixture was stirred at 23° C. for 1.5 hours, tap water (20.00 g) was added thereto, and the mixture was further stirred for 0.5 hours. After adding tap water (50.00 g) thereto over 15 minutes, the mixture was stirred for 2 hours. Thereafter, tap water (70.02 g) was added over 22 minutes, the mixture was stirred for 1.5 hours, and a solid was filtered. The obtained solid was washed with 2-propanol (80 mL) and then dried to obtain compound 5 (27.83 g, 50.55 mmol) as a white solid.

$^1$H-NMR (CDCl$_3$) δ: 7.82-7.88 (m, 4H), 7.70-7.7.76 (m, 4H), 4.40-4.49 (m, 1H), 3.94-4.07 (m, 2H), 3.66-3.80 (m, 3H), 3.38-3.56 (m, 3H), 2.38-2.52 (m, 2H), 0.97-1.01 (m, 12H).

$^{13}$C-NMR (CDCl$_3$) δ: 19.8 (d, J=6.6 Hz), 24.19, 24.24, 24.47, 24.53, 41.2, 41.3, 41.4, 43.0, 43.1, 58.2 (d, J=21.1 Hz), 68.3 (d, J=10.9 Hz), 117.4, 123.2, 123.3, 132.1, 132.2, 133.97, 134.02, 168.0, 168.1.

$^{31}$P-NMR (CDCl$_3$) δ: 149.3

ESI-MS (m/z): 551 (M+1), 573 (M+23).

2) Synthesis of Lipid-Linked Oligonucleotide

The following conditions were used for UPLC analysis.

Mobile phase [A]: 200 mM 1,1,1,3,3,3-hexafluoro-2-propanol, and 8 mM triethylamine-containing aqueous solution, Mobile phase [B]: 200 mM 1,1,1,3,3,3-hexafluoro-2 propanol, and 8 mM triethylamine-containing methanol solution Gradient: linear gradient of solvent FBI from 5% to 26% was performed in 7.29 minutes, and then linear gradient of solvent FBI from 26% to 55% was performed in 1.21 minutes, linear gradient of solvent FBI from 55% to 95% was performed in 3.64 minutes, and 95% solvent FBI was kept for 2.86 minutes.

Column: ACQUITY UPLC (registered trademark) Protein BEH C4, 300 Å (1.7 μm i.d. 2.1×50 mm) (Waters)

Flow rate: 0.51 mL/min

UV Detection wavelength: 254 nm

Column temperature: 45° C.

[Formula 38]

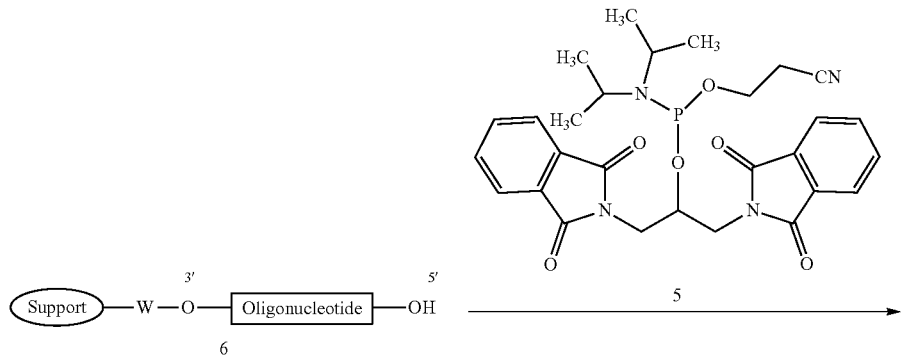

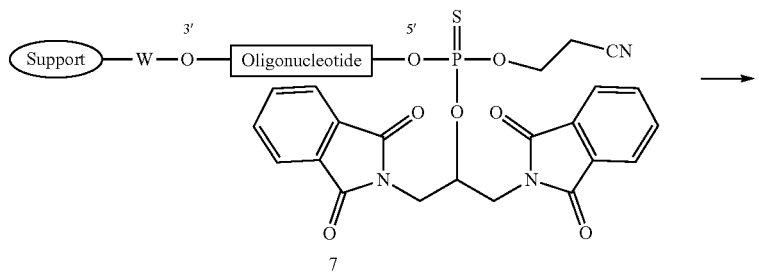

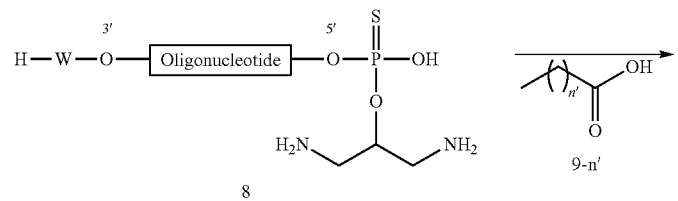

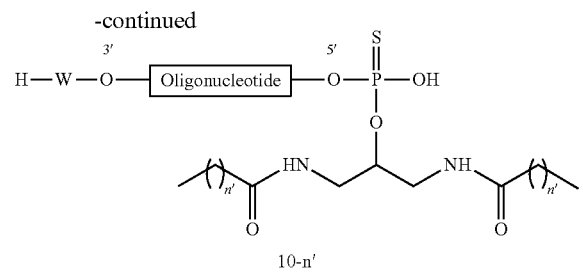

10-n' wherein each symbol has the same meaning as described above, and n' is an integer of 6 to 28.

2-1) Synthesis of Oligonucleotide

The oligonucleotide was synthesized by phosphoramidite method using AKTA Oligopilot 100 (GE Healthcare (Cytiva)), NS-8-I (Dainippon Seiki Co., Ltd.), and NS-8-II (Dainippon Seiki Co., Ltd.) which are automated nucleic acid synthesizers. Coupling time was set to 3 minutes, and 2 equivalents to 10 equivalents of amidite were used for condensation of one monomer. In a final cycle, 5 equivalents of the compound 5 as a monomer to be introduced was prepared into a 0.2 M acetonitrile solution and added to the obtained compound 6, and the coupling time was set to 60 minutes to obtain compound 7.

Incidentally, 0.02 M Oxidizer (Sigma-Aldrich), iodine/pyridine/water/=12.7/9/1 (w/v/v), was used for PO oxidation, and a 0.2 M pyridine solution of xanthane hydride, and acetonitrile/3-picoline 1/1 (v/v), 1/4 (v/v), and acetonitrile/pyridine 1/4 (v/v) solutions of 50 mM DDTT ((dimethylamino-methylidene) amino-3H-1,2,4-dithiazoline-3-thione) were used for PS oxidation. BTT activator (5-benzylthio)-1H-tetrazole) (Sigma-Aldrich) and ETT activator (5-ethylthio)-1H-tetrazole) (Sigma-Aldrich) were used as activators, and CapA and CapB (Sigma-Aldrich) were used as capping reagents. Deb (3 w/v % TCA $CH_2Cl_2$ solution) (Wako Pure Chemical Industries, Ltd.) and Deb (3 w/v % Dichloroacetic acid, Toluene Solution) were used as detritylation reagents.

2-2) Cutting Out From Resin, Deprotection of Base and Phosphoric Acid

Cutting out of compound 8 from a solid phase carrier, deprotection of a benzoyl group protecting an amino group of adenine, an isobutyryl group protecting an amino group of guanine, an acetyl group protecting an amino group of cytosine, and a 2-cyanoethyl group protecting a hydroxy group of phosphoric acid in the oligonucleotide, and deprotection of a phthaloyl group were carried out by stirring vigorously using ammonia water and n-butylamine at room temperature for 4 hours and at 55° C. for 2 hours.

As another method, the mixture was stirred vigorously using ammonia water and benzylamine at room temperature for 4 hours and at 55° C. for 4 hours.

In "2-4) Introduction of lipids", it was revealed that the intended lipid introduction reaction was stopped when amines remained. However, when benzylamine was used, the residual benzylamine could be tracked and managed by washing by liquid separation operation described in this section and a UV detector (254 nm) in the "2-3) Purification of compound 8".

In addition, in the liquid separation operation described in this section, it was efficient to remove amines by washing using methyl tert-butyl ether. Specifically, the resin after being cut out from the reaction mixture was separated by filtration, and the obtained resin was washed with water and methyl tert-butyl ether. The solution obtained by combining the filtrate and the washing liquid was washed with methyl tert-butyl ether by liquid separation operation, and then concentrated under reduced pressure to a weight of about 75% to obtain a crude solution of the compound 8.

2-3) Purification of Compound 8

The crude solution of compound 8 was purified by reverse phase liquid chromatography under the following conditions. The obtained fractions were collected and concentrated under reduced pressure to a weight of about 80% to obtain a solution of compound 8.

Purification Conditions

Mobile phase [A]: 100 mM sodium acetate-containing aqueous solution, Mobile phase [B]: acetonitrile Gradient: 0% solvent [B] was kept for 59 minutes, then linear gradient of solvent [B] from 0% to 5% was performed in 1 minute, linear gradient of solvent [B] from 5% to 90% was performed in 30 minutes, and 95% solvent [B] was kept for 10 minutes.

Column: Triart Prep (registered trademark) C18-S (12 nm, i.d. 10×250 mm) (YMC)

Flow rate: 5 mL/min

UV Detection wavelength: 254 nm

Column temperature: 25° C.

2-4) Introduction of Lipids

Compound 9-n' (for example, n'=18, arachidic acid), N-hydroxysuccinimide, and N,N'-dicyclohexylcarbodiimide were dissolved in N-methylopyrrolidone, and the mixture was stirred at 50° C. for 2 hours, then diluted with N-methylopyrrolidone, and the solution of compound 8 was added thereto. The mixture was stirred at room temperature for 2 hours, then ethanol and a 1 M sodium acetate-containing aqueous solution were added thereto, and a solid was separated by filtration. The obtained solid was washed with ethanol and methyl tert-butyl ether, and the washing liquid was combined with the filtrate.

3) Purification, Desalting, and Lyophilization of Compound 10-n'

The obtained solid is subjected to the same method as that described in E) Purification, F) Desalting of purified oligonucleotide and lyophilization in Example 1 of Patent Document 2 to synthesize compound 10-n'.

4) Preparation of Double-Stranded Oligonucleotide

According to the method described in I) Preparation of double-stranded oligonucleotide in Example 1 of Patent Document 2, an oligonucleotide containing a sequence hybridizable with compound 10-n' is synthesized, and annealed with compound 10-n' to prepare a double-stranded nucleic acid, thereby obtaining compounds XI-1 to XI-6.

TABLE 1

| Double-stranded nucleic acid | Bifurcated Lipid-linked oligonucleotide | Oligonucleotide containing hybridizable sequence |
|---|---|---|
| XI-1 | S-1 | ODN2006 |
| XI-2 | S-2 | ODN2006 |
| XI-3 | S-3 | ODN2006 |
| XI-4 | S-4 | ODN2006 |
| XI-5 | S-5 | ODN2006 |
| XI-6 | S-6 | ODN2006 |

In addition, siRNA-4 and siRNA-5 described in Table 14 of Patent Document 4 are obtained in a similar manner.

Example 2 Physical Properties of Intermediate (Amidite) of Present Invention

Physical properties of the compound 5 and the following comparative compounds (compound 4-18 described in Patent Documents 2 and 3, and compound 5-18 described in Patent Document 4) were compared.

[Formula 39]

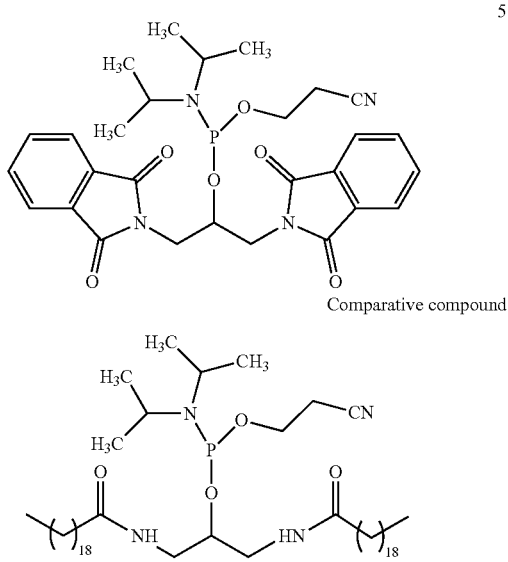

Comparative compound

1) Powder X-Ray Diffraction

Powder X-ray diffraction measurement was performed in accordance with the powder X-ray diffraction measuring method described in General Tests of Japanese Pharmacopoeia. Measurement conditions are shown below.
(Apparatus)
  MiniFlex600 RINT-TTRIII manufactured by Rigaku Corporation
(Operation Method)
  Detector: high-speed one-dimensional detector (D/teX Ultra2) and variable knife edge
  Measuring method: reflection method
  Type of light source: Cu bulb
  Wavelength used: CuKα ray
  Tube current: 15 mA
  Tube voltage: 40 Kv
  Sample plate: non-reflective plate (silicon)
  X-ray incident angle (θ): 4 to 40°, sampling width: 0.02°

(Results)
Compound 5: The following diffraction pattern was observed.
Powder X-ray diffraction 2θ (°): 4.5, 8.9, 9.7, 9.9, 11.4, 12.0, 13.5, 14.3, 18.0, 19.2, 19.5, 20.0, 20.7, 21.7, 21.9, 22.9, 28.9, 29.2
Comparative compound: A broad halo pattern was shown.
2) UV Absorption
Using a detector of liquid chromatography as a photodiode array (PDA) detector, a UV spectrum and a peak area value were measured for a peak corresponding to each compound in the obtained chromatogram, and a relative difference in magnitude of a molar absorbance coefficient of each compound was estimated. Measurement conditions are shown below.
(Apparatus)
  HPLC System: Nexera X2 UHPLC manufactured by Shimadzu Corporation
  Detector: SPD-M30A (PDA), measurement wavelength range: 190 to 400 nm
(Operation Method)
  Compound 5:
  Mobile phase [A]: 10 mM ammonium formate-containing aqueous solution, Mobile phase [B]: acetonitrile
  Gradient: linear gradient from 5% to 95% solvent [B] was performed in 17 minutes, and then 95% solvent [B] was kept for 3 minutes.
  Column: XBridge (registered trademark) Phenyl (3.5 μm, i.d. 4.6×150 mm) (Waters)
  Flow rate: 1.0 mL/min
  Sample solution concentration: about 0.48 mg/mL
  Injection amount: 10 μL
Comparative Compound:
  Mobile phase: 5% acetonitrile-containing aqueous solution
  Column: COSMOSIL (registered trademark) HILIC (5.0 μm, i.d. 4.6×250 mm) (Nacalai Tesque)
  Flow rate: 1.0 mL/min
  Sample solution concentration: about 10 mg/mL
  Injection amount: 1 μL
(Results)
Compound 5: maximum absorption wavelength 221 nm
Comparative compound: maximum absorption wavelength 195 nm (in analysis using a general UV detector, a maximum absorption wavelength is not observed in a practical wavelength range of >210 nm).
The molar absorption coefficient at 221 nm of the compound 5 was estimated to be about 5 times the molar absorption coefficient at 195 nm of the comparative compound. In addition, the molar absorption coefficient at 221 nm of the compound 5 was estimated to be about 40 times the molar absorption coefficient at 221 nm of the comparative compound.
3) Stability
The following conditions were used for the analysis of compound 5.
Mobile phase [A]: 60 mM ammonia-ammonium acetate-containing buffer solution (pH 8.0), Mobile phase [B]: acetonitrile
Gradient: 15% solvent [B] was kept for 0.5 minutes, then linear gradient from 15% to 50% solvent [B] was performed in 2.5 minutes, linear gradient from 50% to 65% solvent [B] was performed in 9 minutes, linear gradient from 65% to 95% solvent [B] was performed in 3 minutes, and 95% solvent [B] was kept for 1 minute.
Column: ACQUITY UPLC (registered trademark) BEH Phenyl (1.7 μm, i.d. 2.1×100 mm) (Waters)
Flow rate: 0.3 mL/min UV Detection wavelength: 295 nm The following conditions were used for the analysis of comparative compound.

Mobile phase [A]: 10 mM ammonium formate-containing aqueous solution, Mobile phase [B]: methanol Gradient: 97% solvent [B] was kept for 20 minutes.

Column: Triart (registered trademark) C8 (3 μm, i.d. 4.6×100 mm) (YMC)

Flow rate: 1.0 mL/min

Injection amount: 10 μL

Detector: Corona CAD, Corona CAD detection conditions: 60 Hz, BCD polarity+, pressure 35±1 psi, total flow rate 1.53 mL/min (Results)

Compound 5 (40° C.): 99.6% (initial)→99.6% (after 7 days)→99.7% (after 50 days)

Comparative compound (−20° C.): 54.3% (initial)→42.0% (after 71 days)→33.8% (after 7 months)

INDUSTRIAL APPLICABILITY

By using the production method of the present invention, a high-quality bifurcated lipid-linked oligonucleotide can be efficiently produced. The intermediate of the present invention is particularly useful in the production method.

---

The invention claimed is:

1. A compound of formula (I):

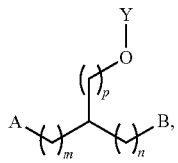

wherein
A and B are each independently

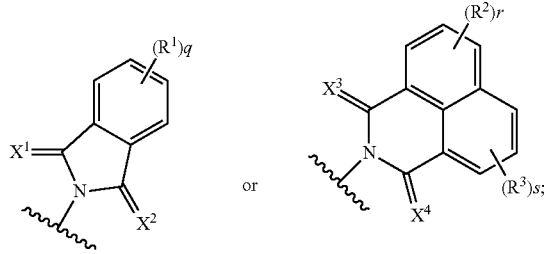

$X^1$, $X^2$, $X^3$, and $X^4$ are each independently O or S;
q are each independently an integer of 0 to 4;
r and s are each independently an integer of 0 to 3;
$R^1$, $R^2$, and $R^3$ are each independently halogen, hydroxy, substituted or unsubstituted alkyl, substituted or unsubstituted alkenyl, or substituted or unsubstituted alkynyl; provided that $R^1$ of $(R^1)q$, $R^2$ of $(R^2)r$, and $R^3$ of $(R^3)s$ may be the same or different; and
m, n and p are each independently an integer of 0 to 5;
Y is
a group of formula (Y-1): —P(OR$^4$)(N(R$^5$)$_2$), wherein $R^4$ is substituted or unsubstituted alkyl, and R's are each independently substituted or unsubstituted alkyl,
a group of formula (Y-2): —P(=R$^6$)(OR$^7$)$_2$, wherein $R^6$ is O or S, and $R^7$ are each independently a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or
a group of formula (Y-3): —P(=R$^8$)H(OR$^9$), wherein $R^8$ is O or S, and $R^9$ is a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or its salt.

2. The compound or its salt according to claim 1, wherein A and B are each independently

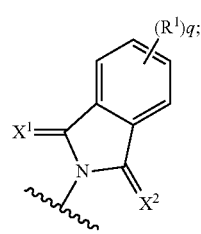

$X^1$ and $X^2$ are O; and
Y is a group of the formula (Y-1).

3. The compound or its salt according to claim 1, wherein the compound is of the following formula

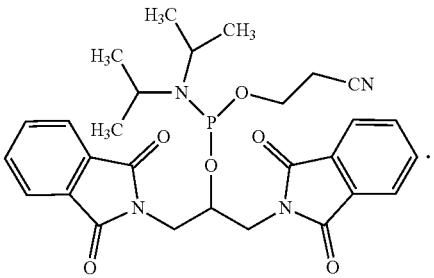 [SMILES: CC(C)N(C(C)C)P(OCCC#N)OC(CN1C(=O)c2ccccc2C1=O)CN1C(=O)c2ccccc2C1=O ; "."]

4. A method for producing a compound of formula (VII):

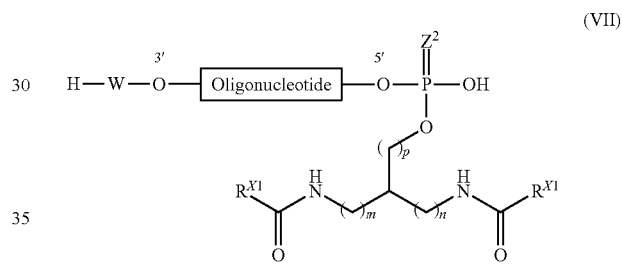

wherein
Oligonucleotide means an oligonucleotide, 3' means a 3' end of the oligonucleotide, and 5' means a 5' end of the oligonucleotide, W is a single bond or a compound of a formula:

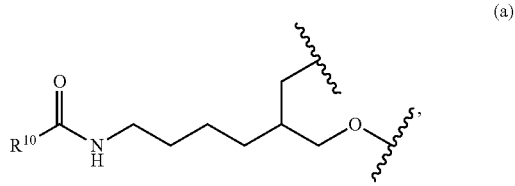

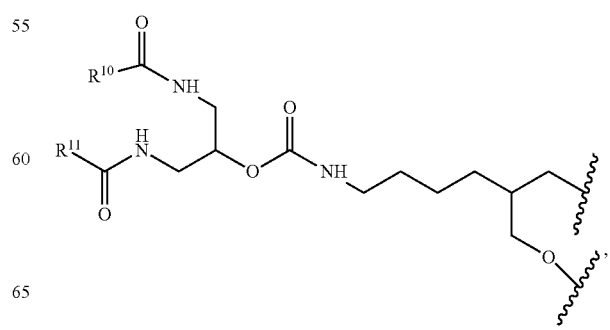

-continued

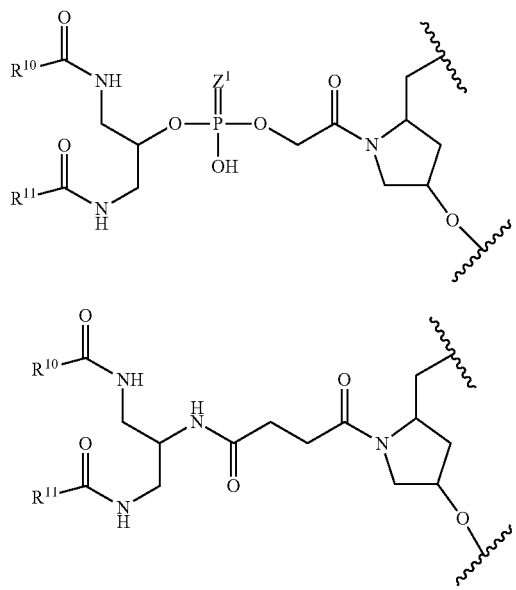

(c)

or (d)

wherein $Z^1$ is O or S;
$R^{10}$ and $R^{11}$ are each independently alkyl or alkenyl;
terminal alkylene in the formula is bonded to oxygen at the 3' end of the oligonucleotide, and a terminal oxygen atom in the formula is bonded to a solid phase carrier;
$Z^2$ is
O or S when Y in formula (II) is a group of formula (Y-1), $R^6$ when Y in formula (II) is a group of formula (Y-2), and $R^8$ when Y in formula (II) is a group of formula (Y-3); and
m, n and p are each independently an integer of 0 to 5; and $R^{X1}$ is alkyl or alkenyl,
comprising steps of
reacting a compound of formula (II):

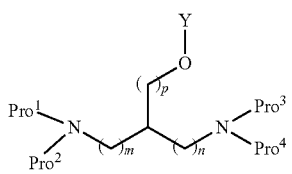

(II)

wherein
$Pro^1$, $Pro^2$, $Pro^3$ and $Pro^4$ are each independently a protecting group;
$Pro^1$ and $Pro^2$ or $Pro^3$ and $Pro^4$ may be taken together to form a protecting group;
m, n and p have the same meaning as described above; and
Y is
a group of formula (Y-1): $-P(OR^4)(N(R^5)_2)$, wherein $R^4$ is substituted or unsubstituted alkyl, and $R^5$s are each independently substituted or unsubstituted alkyl,
a group of formula (Y-2): $-P(=R^6)(OR^7)_2$, wherein $R^6$ is O or S, and $R^7$ are each independently a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or a group of formula (Y-3): $-P(=R^8)H(OR^9)$, wherein $R^8$ is O or S, and $R^9$ is a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl,
with an oligonucleotide of formula (III):

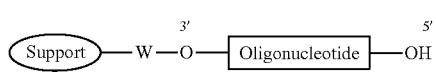

(III)

wherein Support means a solid phase carrier, and Oligonucleotide, 3', 5', and W have the same meaning as described above,
to obtain a compound of formula (IV):

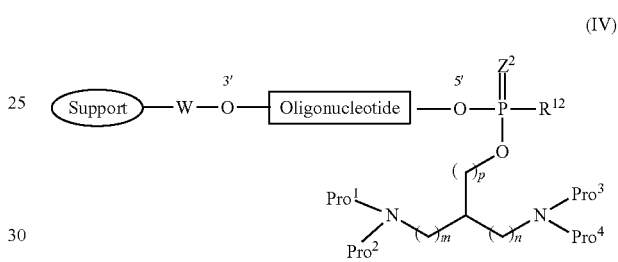

(IV)

wherein
$R^{12}$ is
$OR^4$ when Y in formula (II) is a group of formula (Y-1),
$OR^7$ when Y in formula (II) is a group of formula (Y-2), and
$OR^9$ when Y in formula (II) is a group of formula (Y-3); and
Support, Oligonucleotide, 3', 5', W, $Z^2$, $Pro^1$, $Pro^2$, $Pro^3$, $Pro^4$, m, n, and p have the same meaning as described above,
deprotecting a protecting group in the compound of formula (IV) and cutting out from a solid phase carrier, in the presence of a cleavage reagent and a deprotecting agent,
to obtain a compound of formula (V):

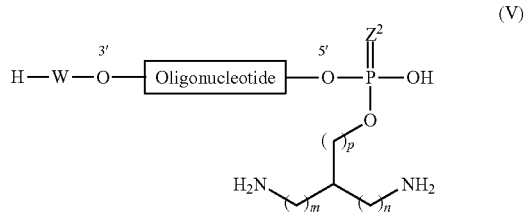

(V)

wherein each symbol has the same meaning as described above, and when W is any of the groups of the formulae (a) to (d), a terminal oxygen atom in the formulae (a) to (d) is bonded to a hydrogen atom; and
reacting a compound of formula (VI): $R^{X1}-C(=O)-L^1$, wherein $R^{X1}$ has the same meaning as described above, and $L^1$ is OH or a leaving group
with the compound of formula (V).

5. A method for producing a compound of formula (X):

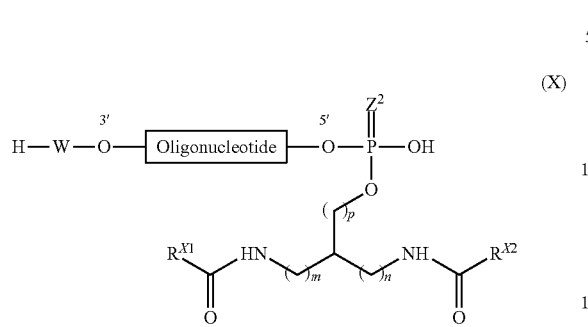

wherein

Oligonucleotide means an oligonucleotide, 3' means a 3' end of the oligonucleotide, and 5' means a 5' end of the oligonucleotide, W is a single bond or a compound of a formula:

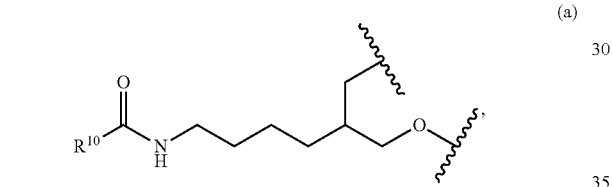

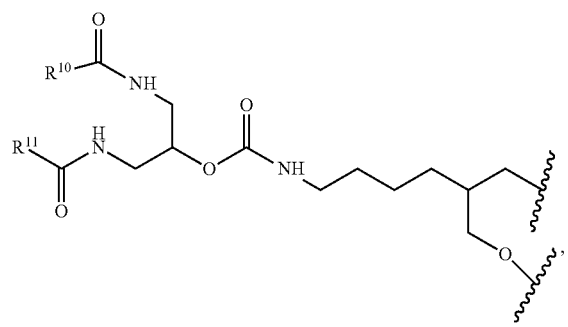

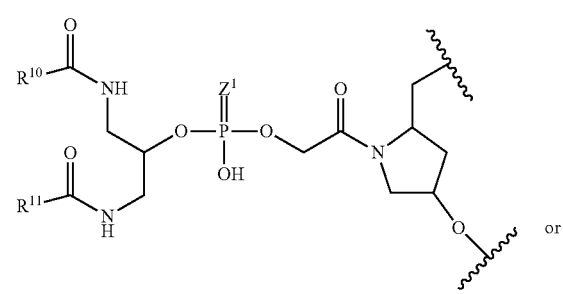 or

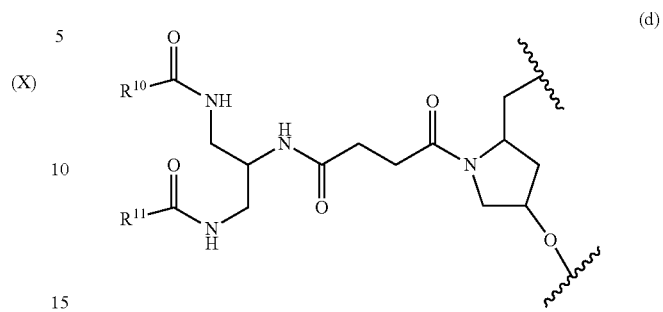

wherein $Z^1$ is O or S;
$R^{10}$ and $R^{11}$ are each independently alkyl or alkenyl;
terminal alkylene in the formula is bonded to oxygen at the 3' end of the oligonucleotide, and a terminal oxygen atom in the formula is bonded to a solid phase carrier;
$Z^2$ is
O or S when Y in formula (II) is a group of formula (Y-1),
$R^6$ when Y in formula (II) is a group of formula (Y-2), and
$R^8$ when Y in formula (II) is a group of formula (Y-3); and
m, n and p are each independently an integer of 0 to 5;
$R^{X1}$ is alkyl or alkenyl; and
$R^{X2}$ is alkyl or alkenyl;
comprising steps of reacting a compound of formula (II):

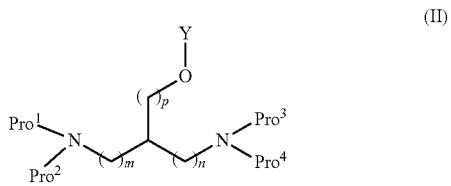

wherein
$Pro^1$, $Pro^2$, $Pro^3$ and $Pro^4$ are each independently a protecting group;
$Pro^1$ and $Pro^2$ or $Pro^3$ and $Pro^4$ may be taken together to form a protecting group;
m, n and p have the same meaning as described above;
Y is
a group of formula (Y-1): —P(OR$^4$)(N(R$^5$)$_2$), wherein $R^4$ is substituted or unsubstituted alkyl, and $R^5$ are each independently substituted or unsubstituted alkyl,
a group of formula (Y-2): —P(=R$^6$)(OR$^7$)$_2$, wherein $R^6$ is O or S, and $R^7$ are each independently a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, or
a group of formula (Y-3): —P(=R$^8$)H(OR$^9$), wherein $R^8$ is O or S, and $R^9$ is a hydrogen atom, substituted or unsubstituted alkyl, substituted or unsubstituted alkenyl, substituted or unsubstituted alkylcarbonyl, substituted or unsubstituted aromatic carbocyclyl, or substituted or unsubstituted aromatic carbocyclylcarbonyl, with an oligonucleotide of formula (III):

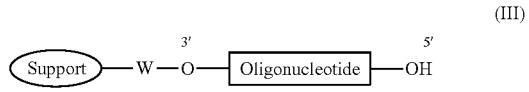
(III)

wherein Support means a solid phase carrier, and Oligonucleotide, 3', 5', and W have the same meaning as described above, to obtain a compound of formula (IV):

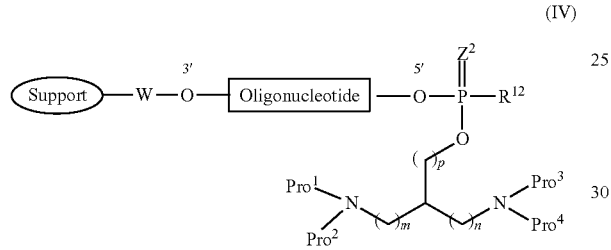
(IV)

wherein $R^{12}$ is $OR^4$ when Y in formula (II) is a group of formula (Y-1), $OR^7$ when Y in formula (II) is a group of formula (Y-2), and $OR^9$ when Y in formula (II) is a group of formula (Y-3); and Support, Oligonucleotide, 3', 5', W, $Z^2$, $Pro^1$, $Pro^2$, $Pro^3$, $Pro^4$, m, n, and p have the same meaning as described above, deprotecting a protecting group in the compound of formula (IV) and cutting out from a solid phase carrier, in the presence of a cleavage reagent and a deprotecting agent, to obtain a compound of formula (V):

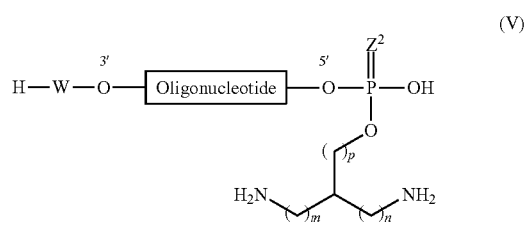
(V)

wherein each symbol has the same meaning as described above, and when W is any of the groups of the formulae (a) to (d), a terminal oxygen atom in the formulae (a) to (d) is bonded to a hydrogen atom;

reacting a compound of formula (VI): $R^{X1}$—C(=O)-$L^1$, wherein $R^{X1}$ has the same meaning as described above, and $L^1$ is OH or a leaving group with the compound of formula (V), to obtain a compound of formula (VIII):

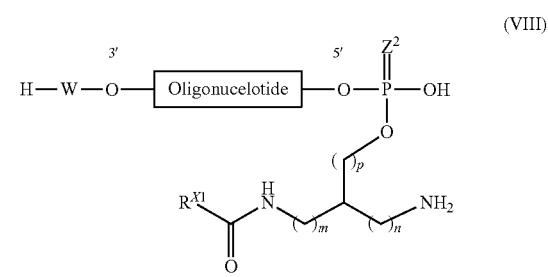
(VIII)

wherein each symbol has the same meaning as described above; and reacting a compound of formula (IX): $R^{X2}$—C(=O)-$L^2$, wherein $R^{X2}$ has the same meaning as described above, and $L^2$ is OH or a leaving group with the compound of formula (VIII).

6. The production method according to claim 5, characterized in that $R^{X1}$ is C8 to C30 alkyl or C8 to C30 alkenyl;

$R^{X2}$ is C1 to C29 alkyl or C2 to C29 alkenyl; and the number of carbon atoms of the alkyl or alkenyl of $R^{X2}$ is smaller than the number of carbon atoms of the alkyl or alkenyl of $R^{X1}$.

7. The method according to claim 4, wherein the cleavage reagent and the deprotecting agent contain butylamine and/or benzylamine.

8. The method according to claim 4, comprising a step of washing the compound (V) with an organic solvent.

9. A method for producing a double-stranded oligonucleotide, comprising steps of:

obtaining the compound (VII) by the method according to claim 4, and annealing an oligonucleotide comprising a sequence capable of hybridizing to an oligonucleotide of the compound (VII) to form a double strand.

10. The method according to claim 9, wherein the double-stranded oligonucleotide is a double-stranded oligonucleotide composed of a chain of a formula:
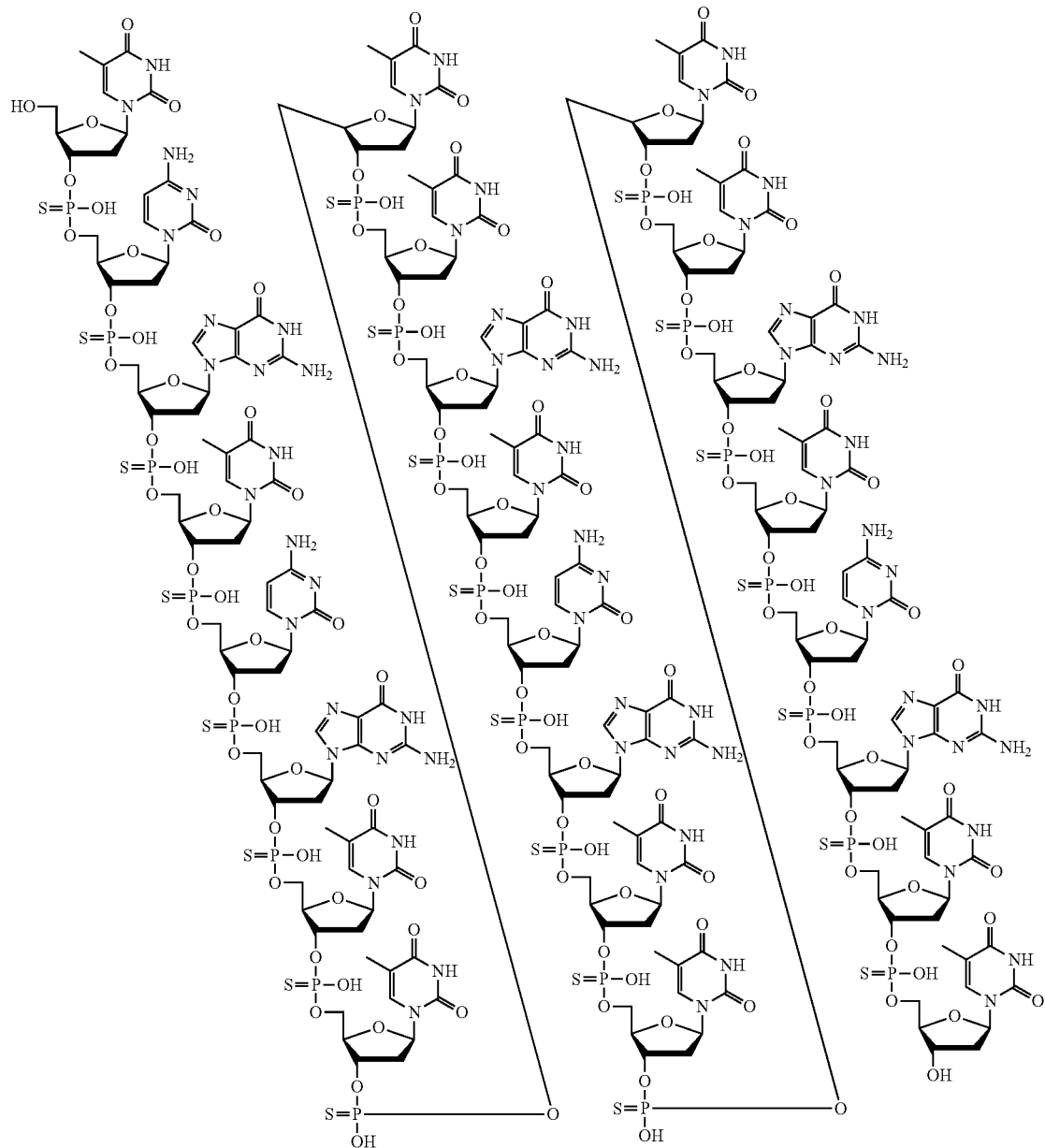
(ODN2006)

and a chain of a formula selected from the following:
a formula:
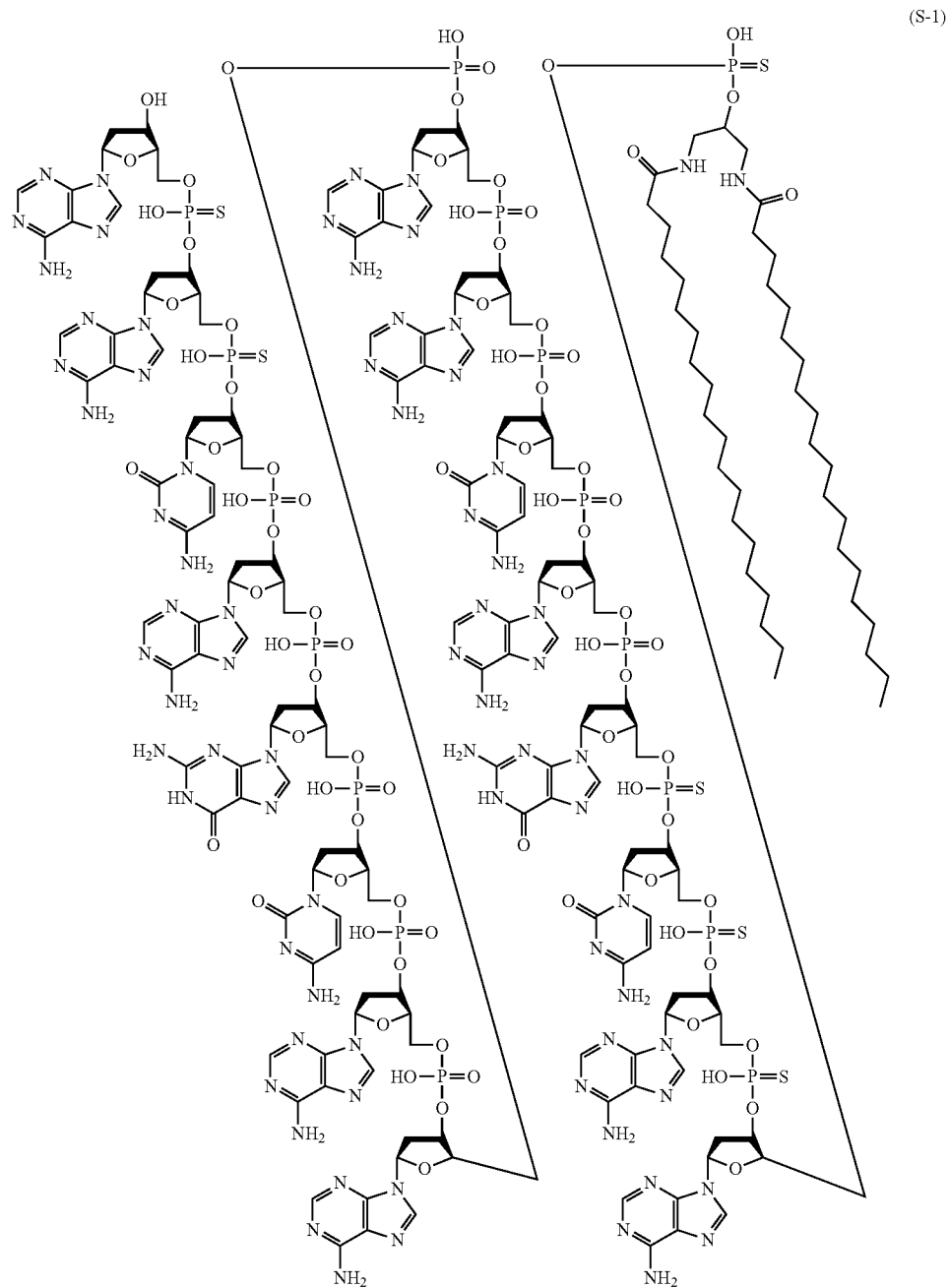
(S-1)

a formula:
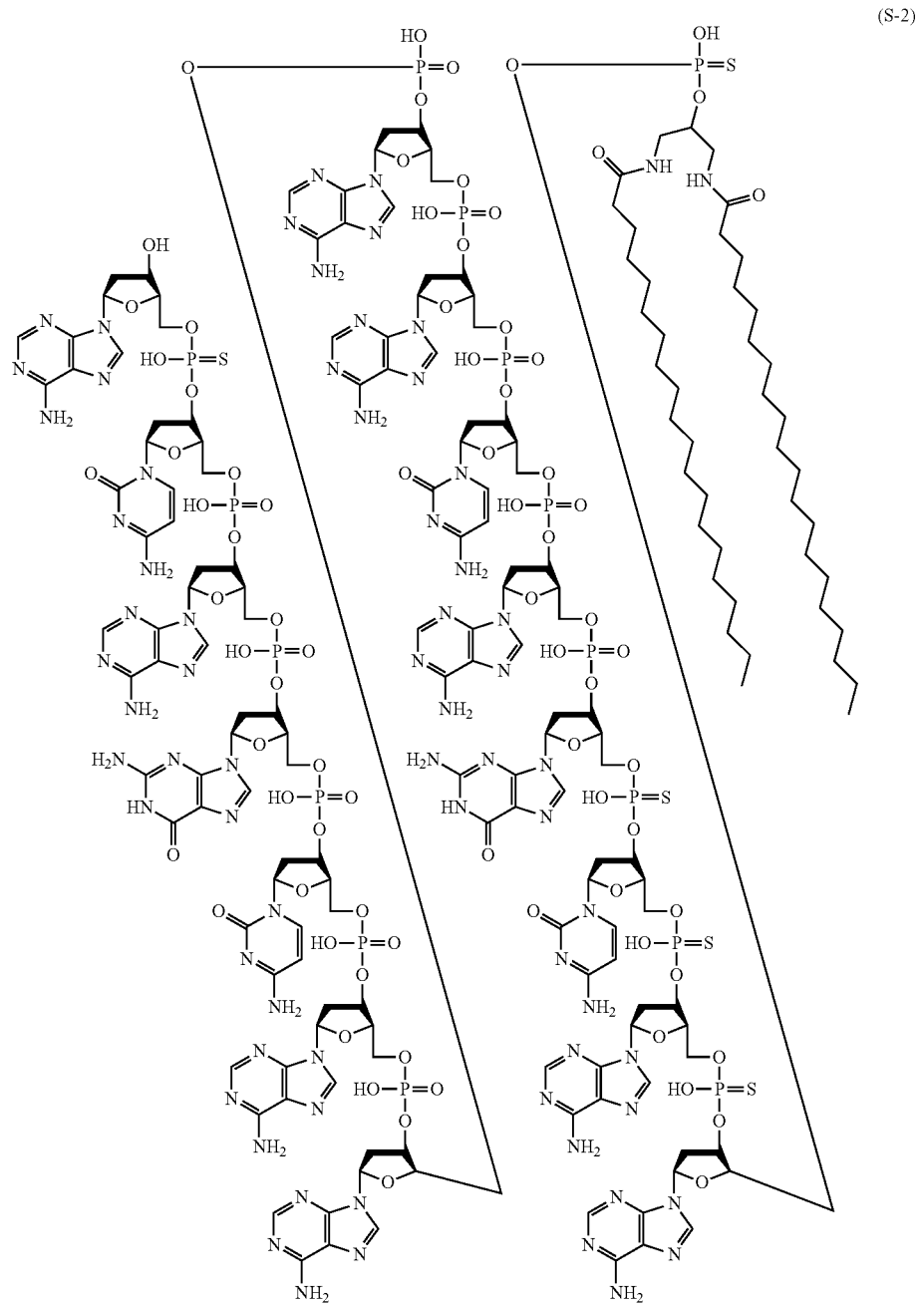
(S-2)

a formula:
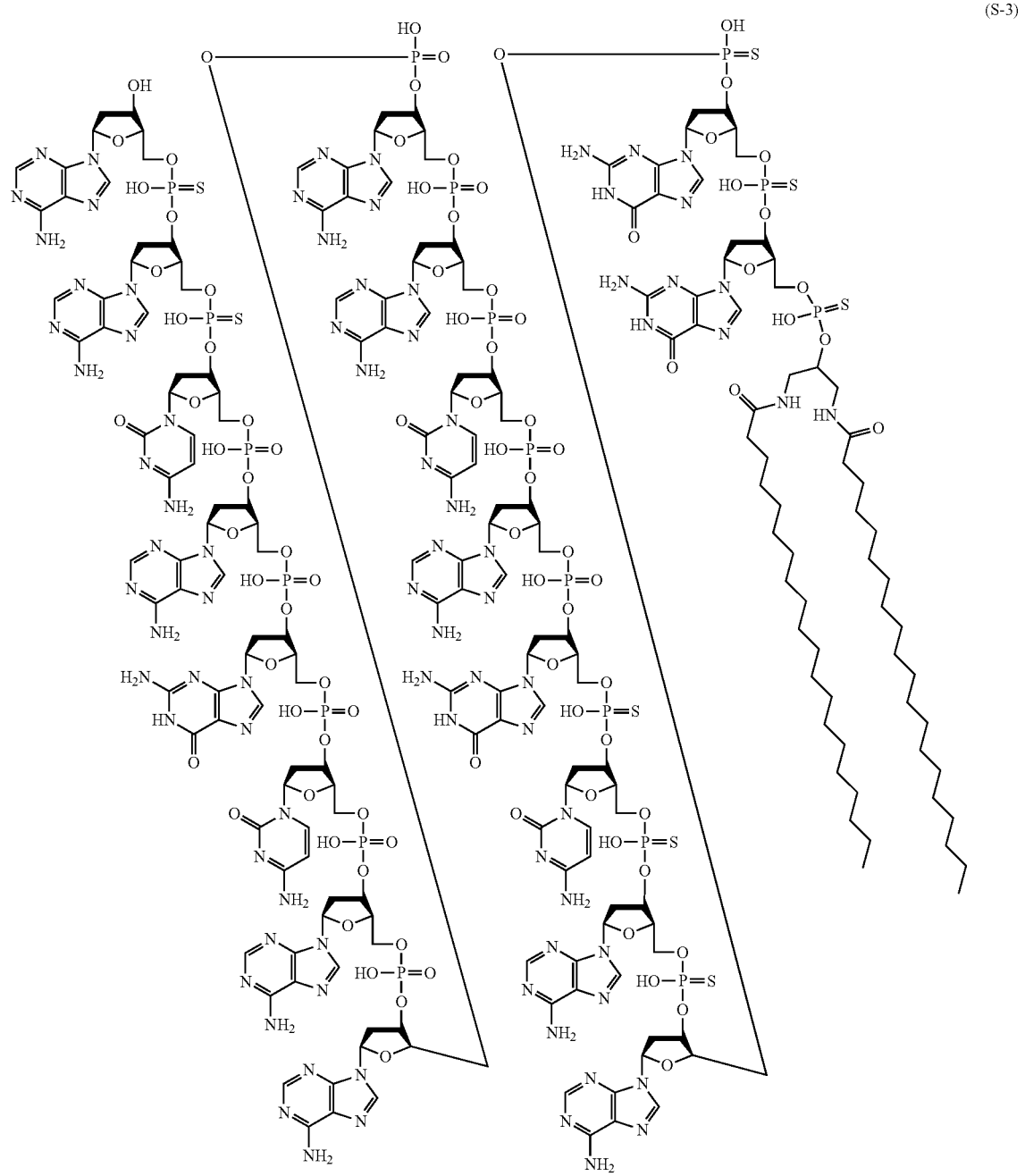
(S-3)

a formula:
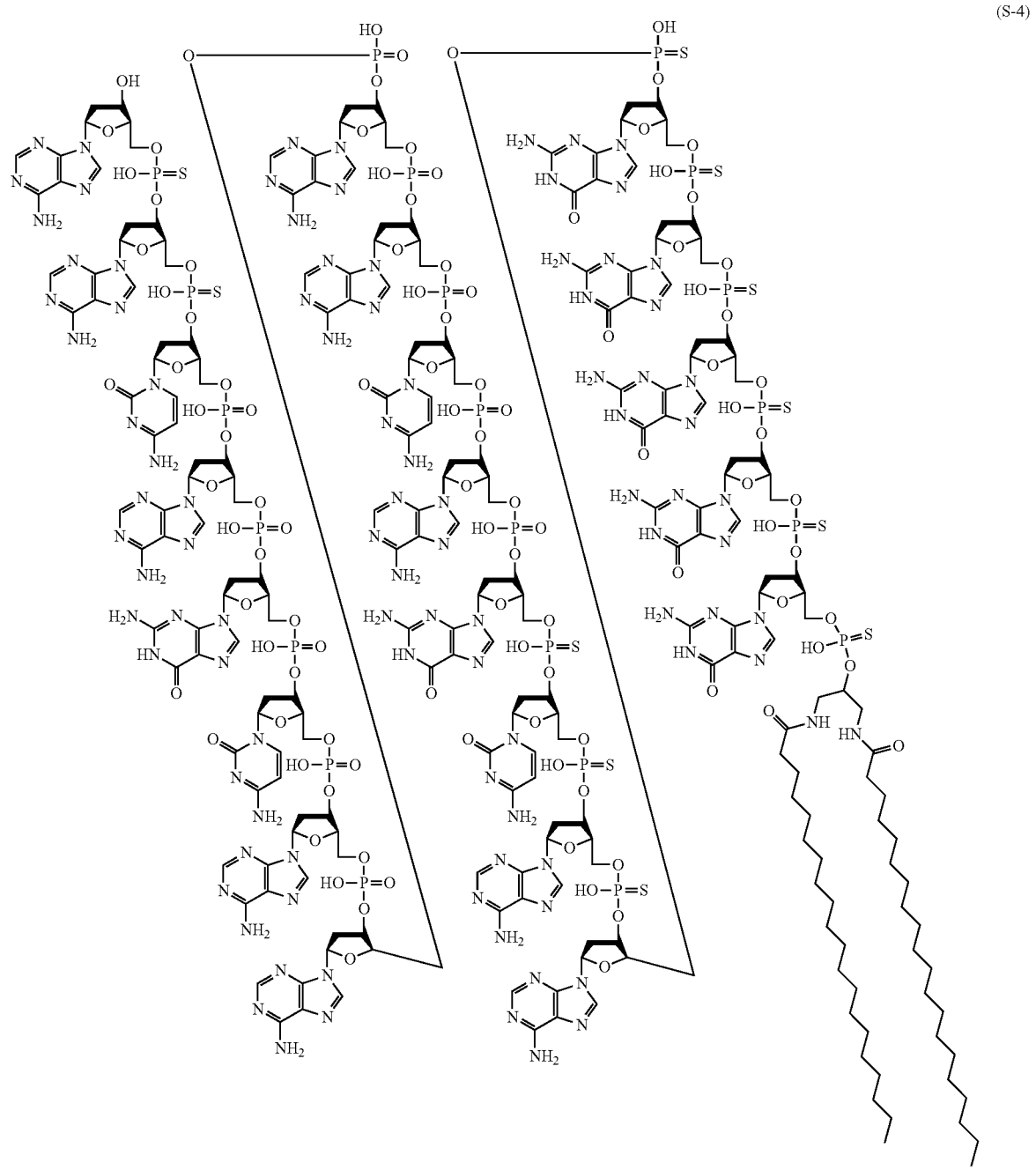
(S-4)

a formula:
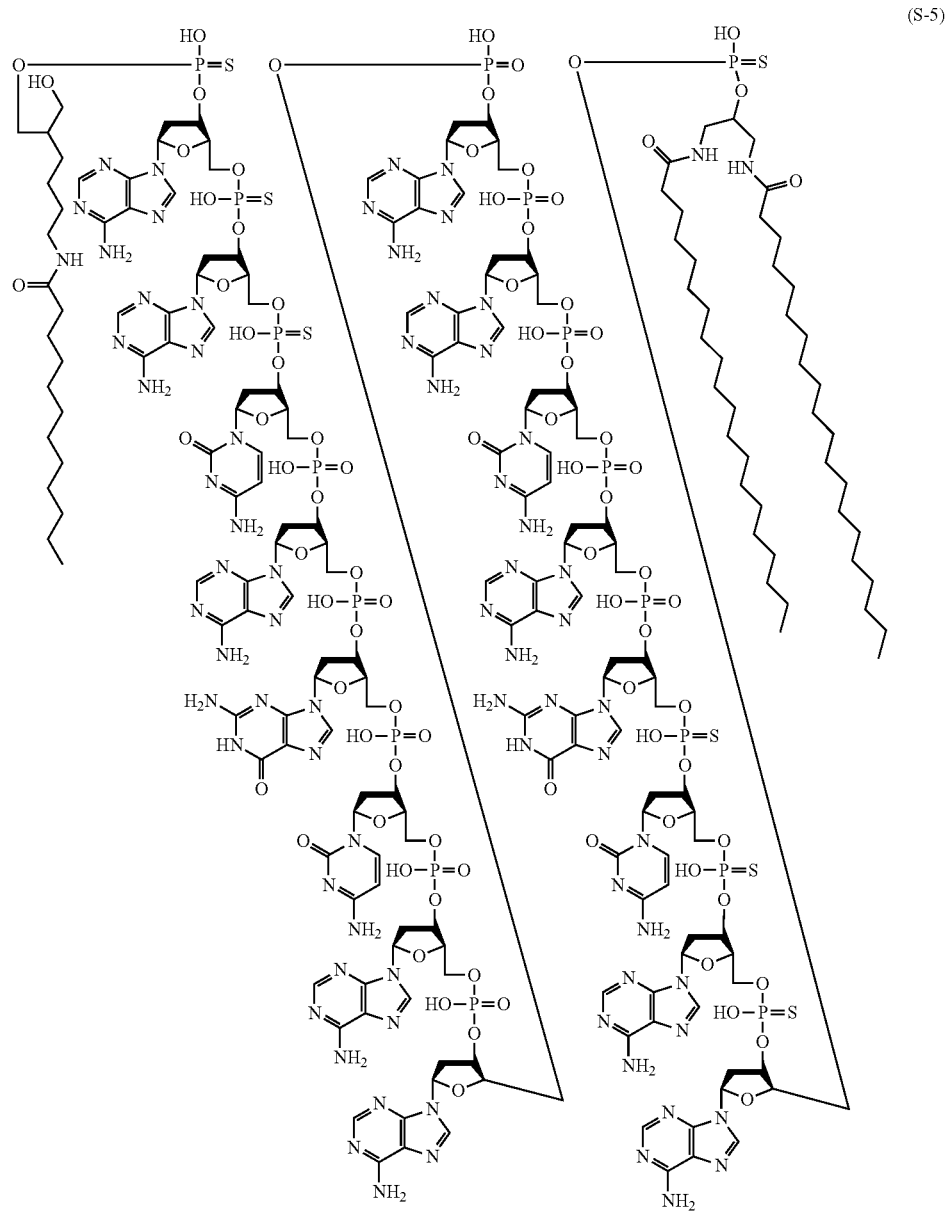
(S-5)

and a formula:

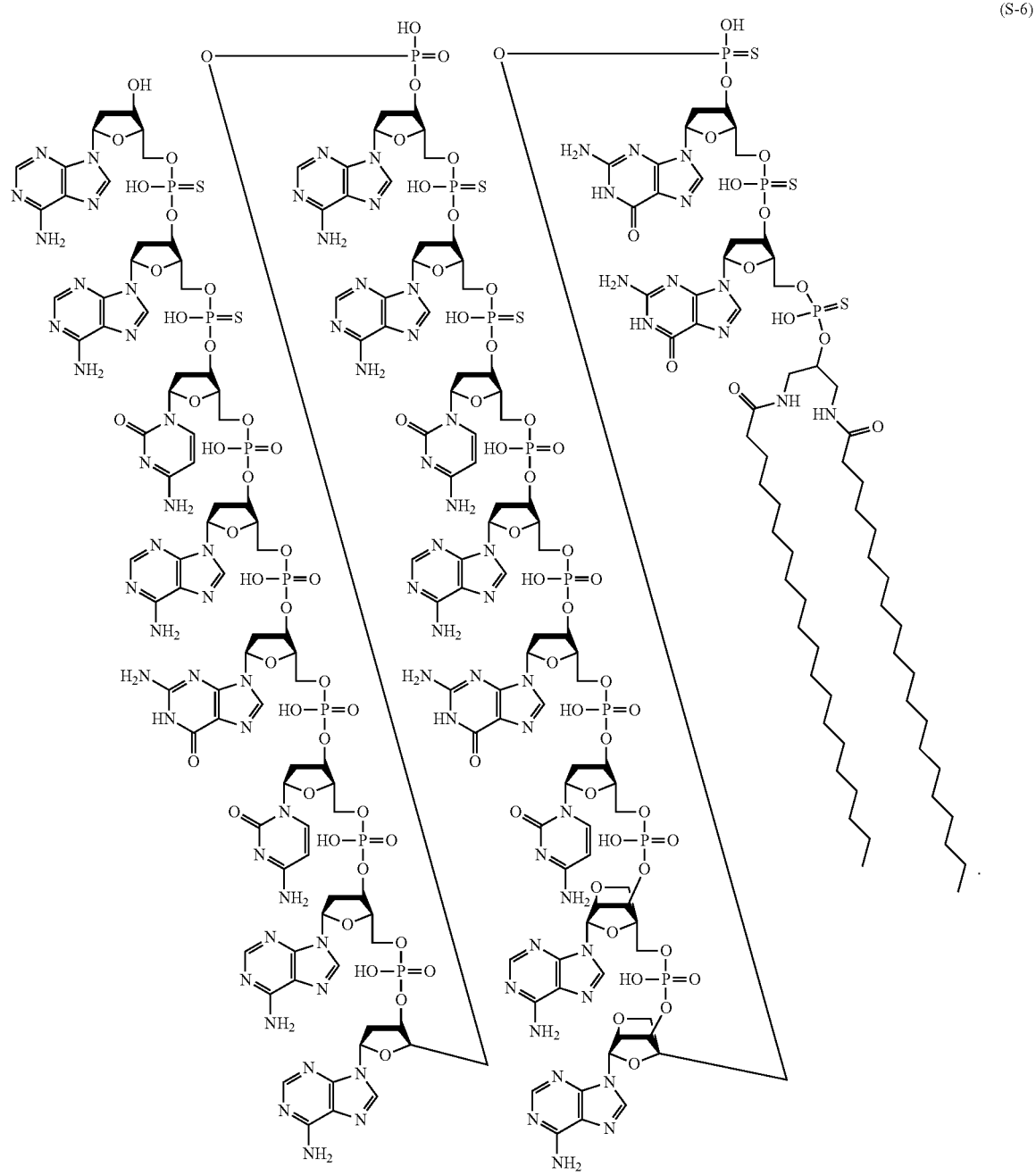

(S-6)

11. The method according to claim 5, wherein the cleavage reagent and the deprotecting agent contain butylamine and/or benzylamine.

12. The method according to claim 5, comprising a step of washing the compound (V) with an organic solvent.

13. A method for producing a double-stranded oligonucleotide, comprising steps of:

obtaining the compound (X) by the method according to claim 5, and annealing an oligonucleotide comprising a sequence capable of hybridizing to an oligonucleotide of the compound (X) to form a double strand.
14. The method according to claim 13, wherein the double-stranded oligonucleotide is a double-stranded oligonucleotide composed of a chain of a formula:
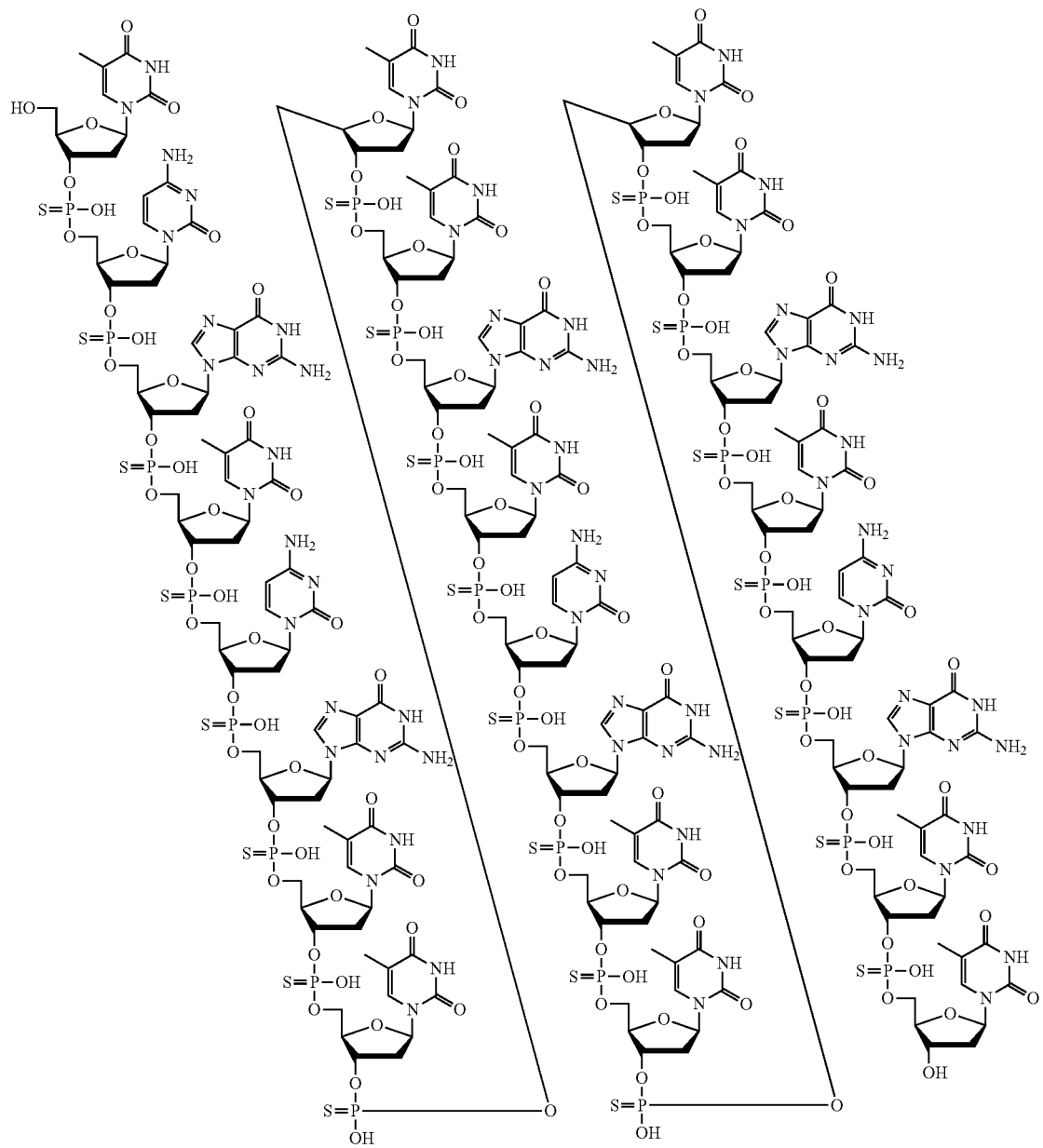
(ODN2006)

a formula:
and a chain of a formula selected from the following:
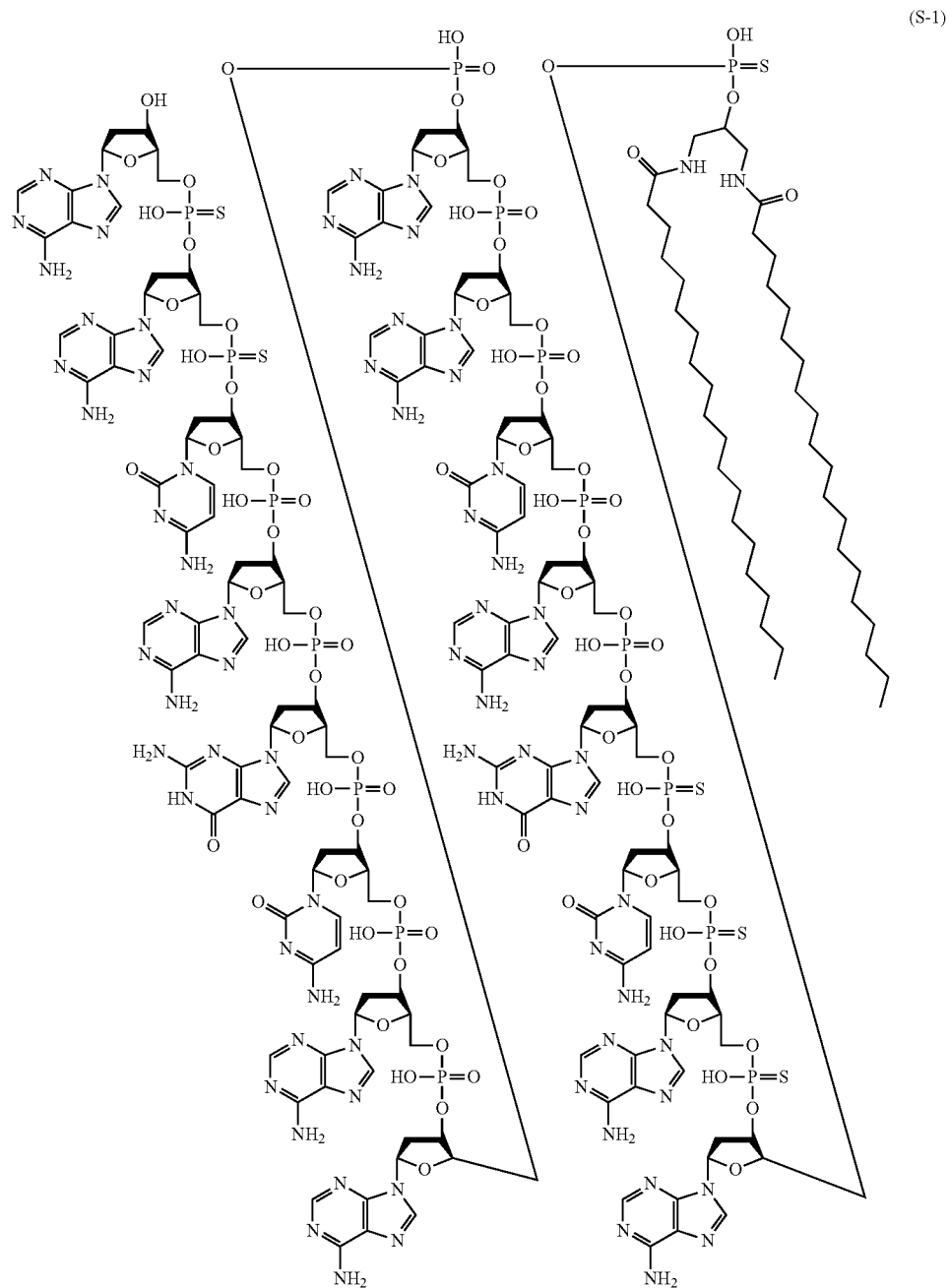
(S-1)

a formula:
and a chain of a formula selected from the following:
a formula:
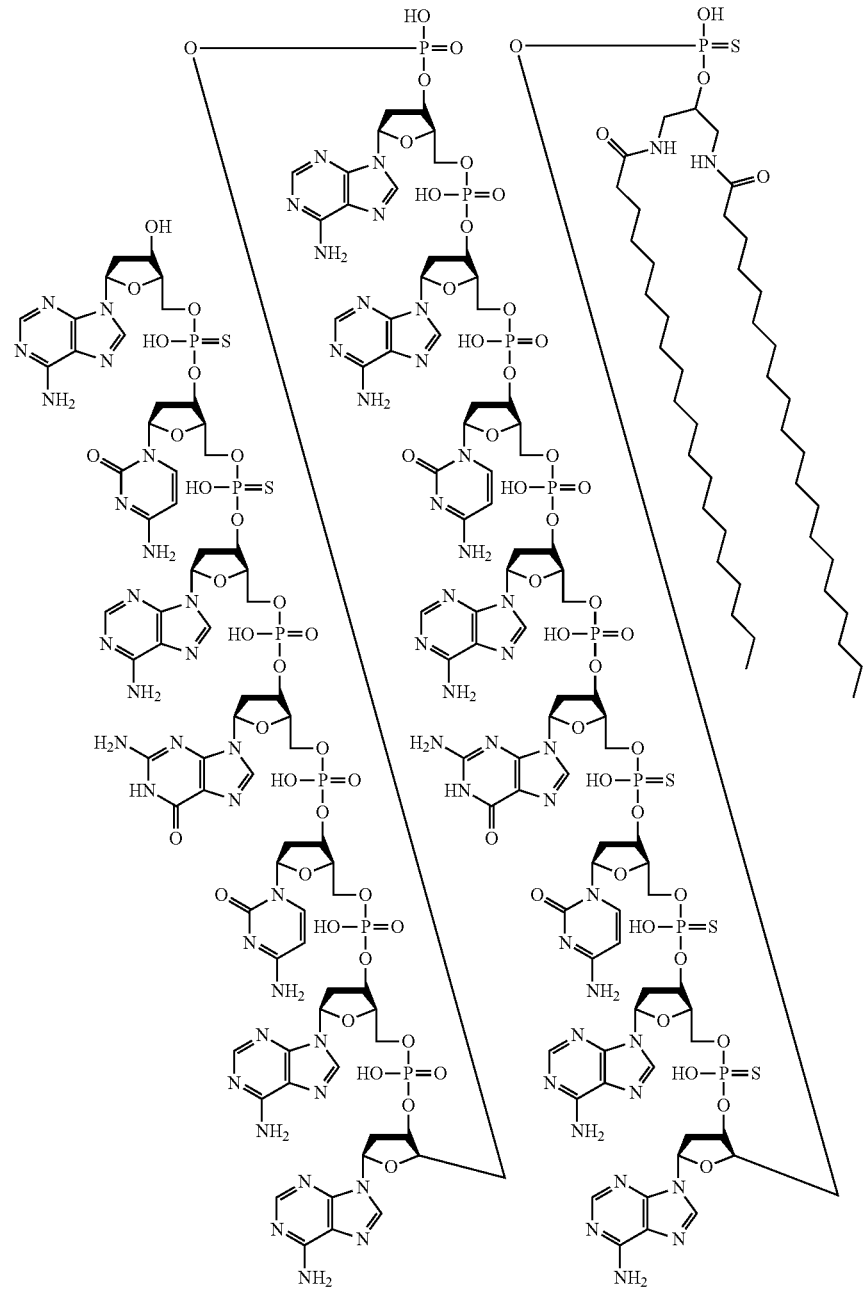
(S-2)

a formula:
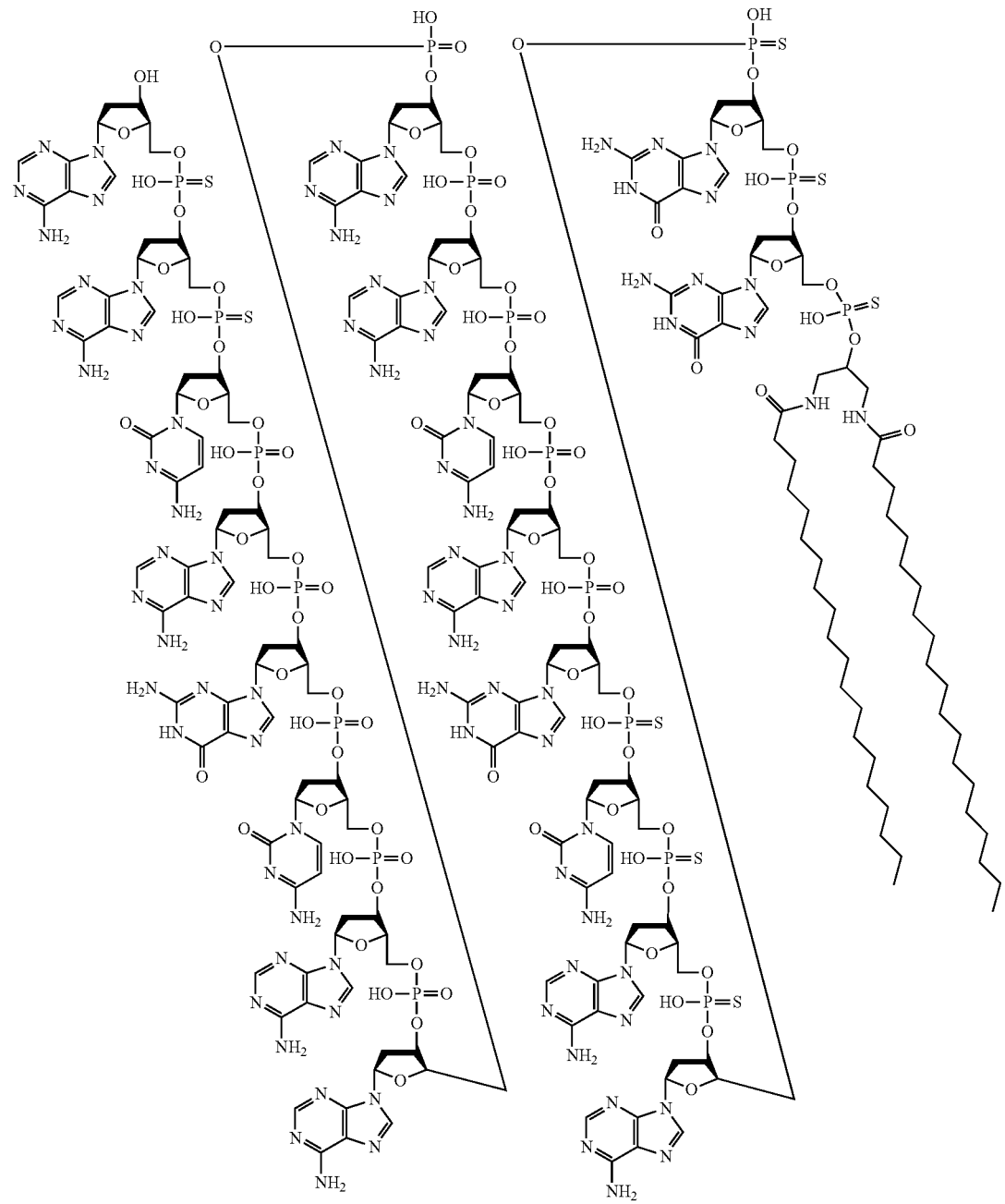
(S-3)

a formula:
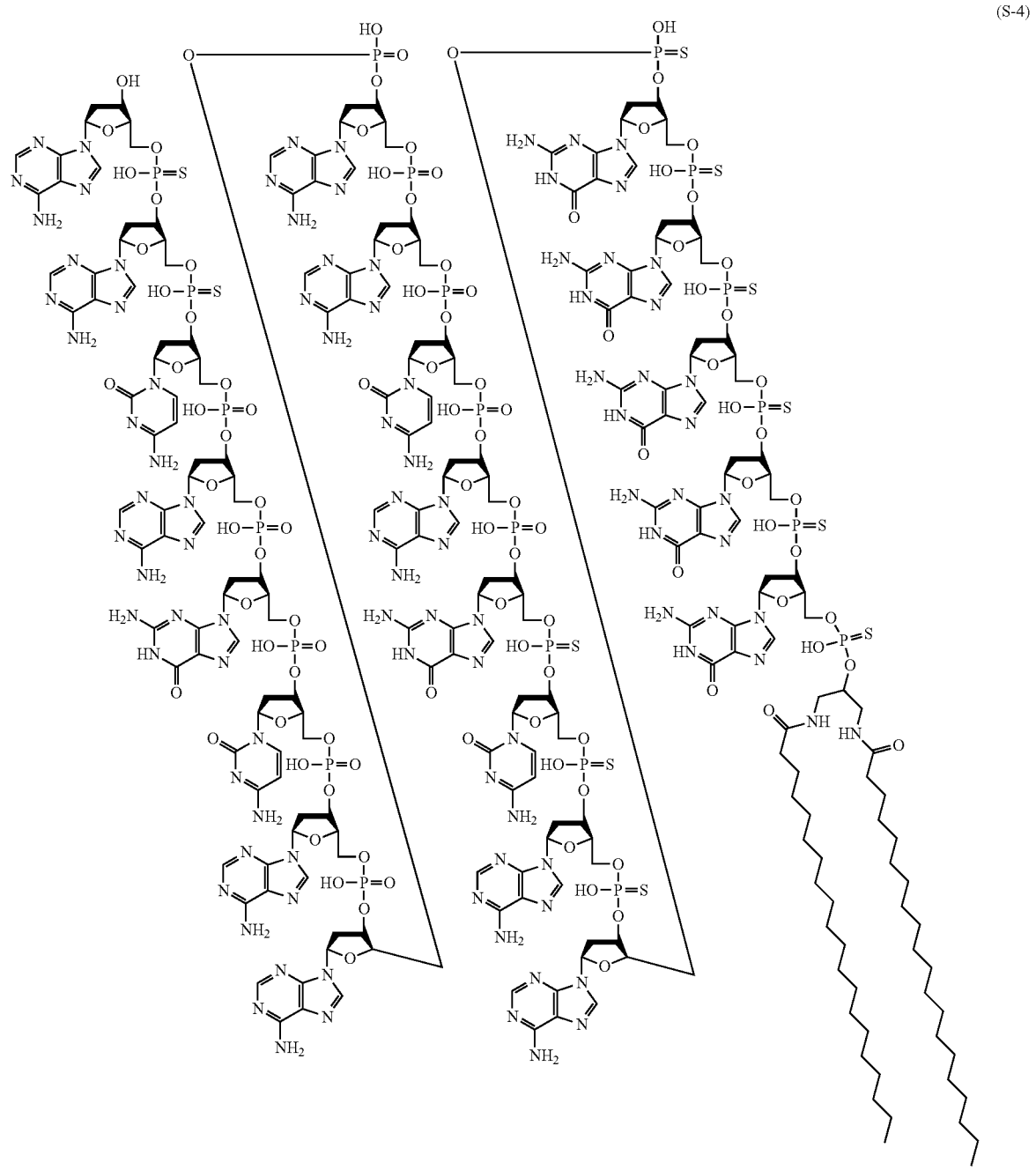
(S-4)

a formula:
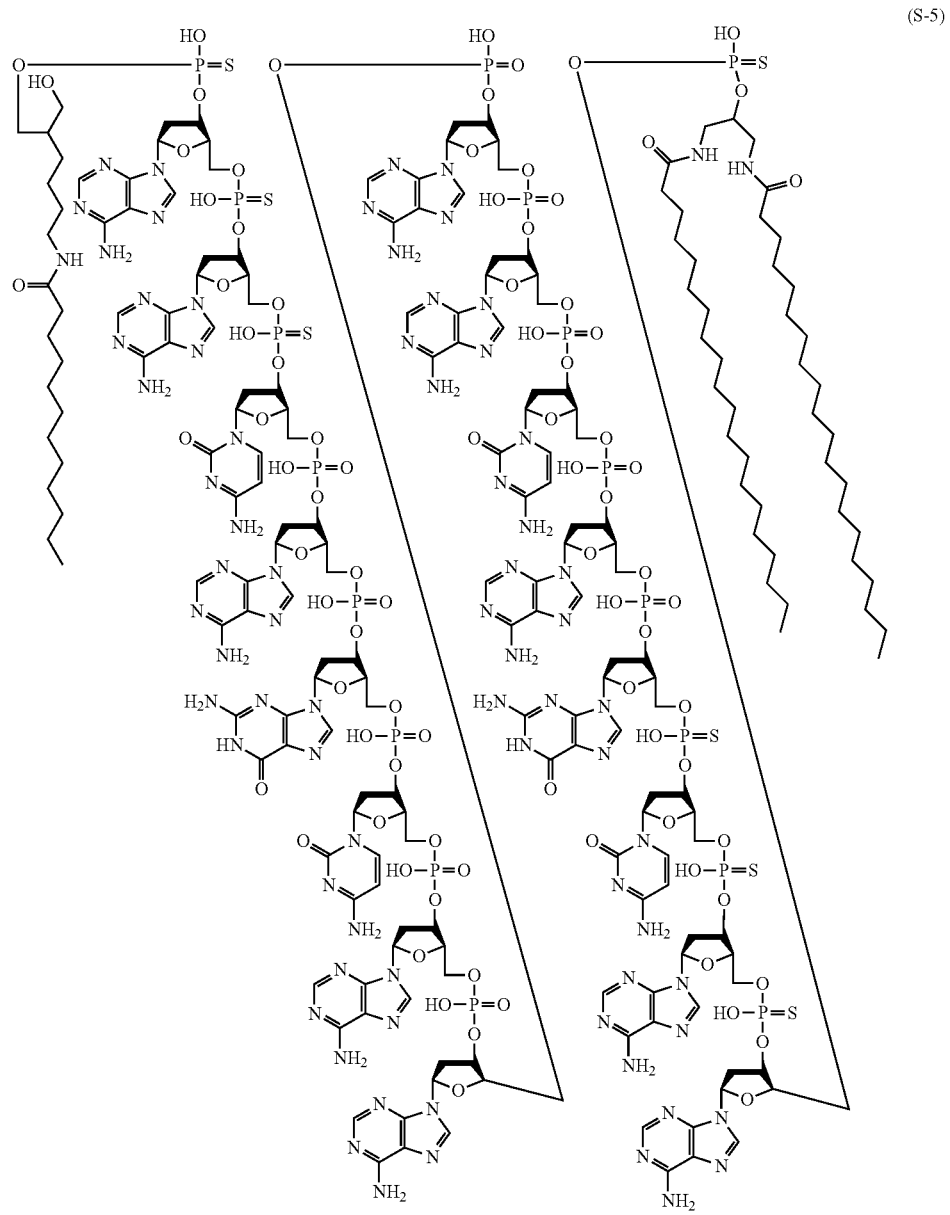
(S-5)

and a formula:
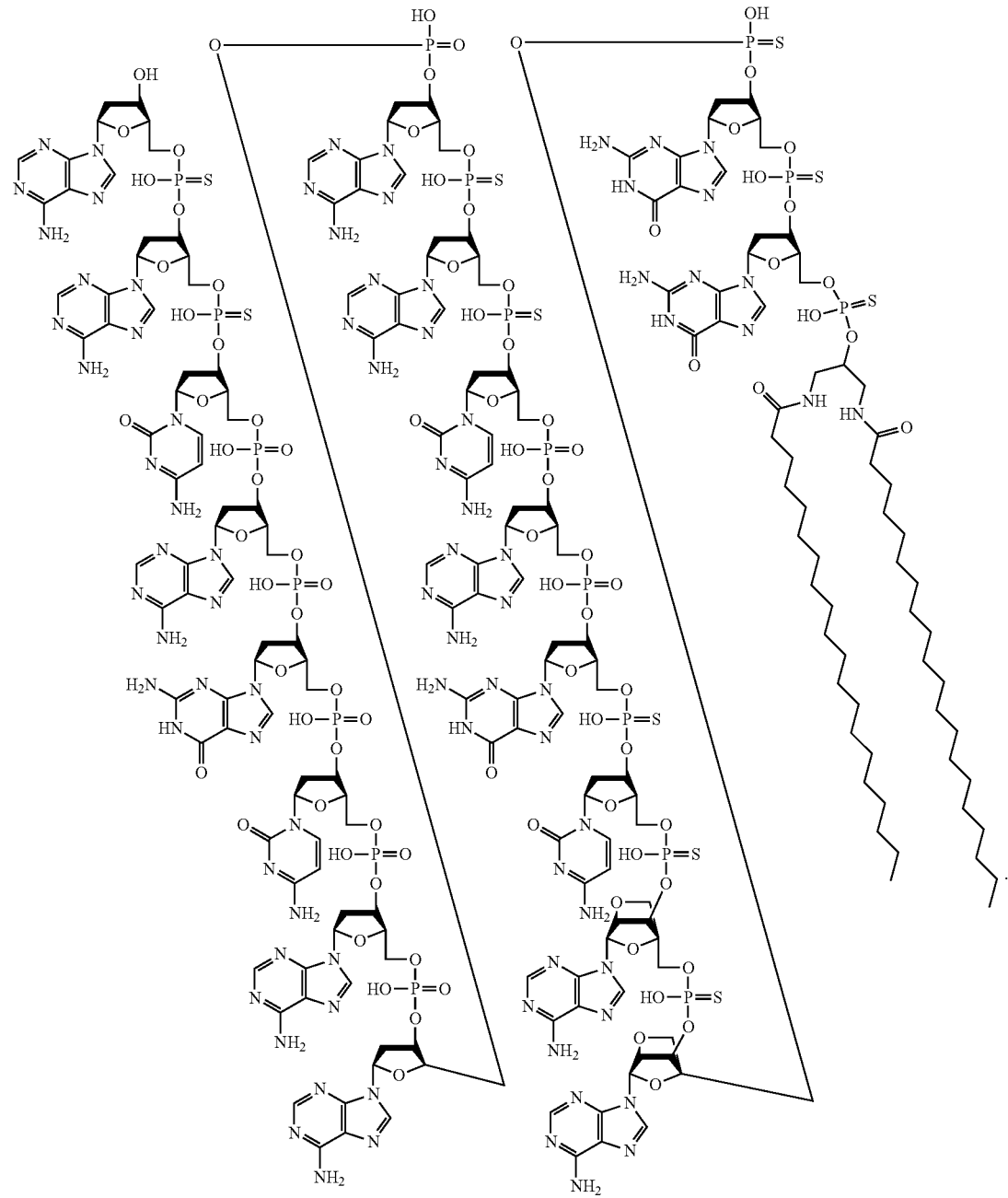
(S-6)
* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial sequence
<220> FEATURE:
<223> OTHER INFORMATION: ODN2006

<400> SEQUENCE: 1
tcgtcgtttt gtcgttttgt cgtt                                          24

<210> SEQ ID NO 2
<211> LENGTH: 16
<212> TYPE: DNA
<213> ORGANISM: Artificial sequence
<220> FEATURE:
<223> OTHER INFORMATION: oligonucleotide

<400> SEQUENCE: 2
aacgacaaaa cgacaa                                                   16

<210> SEQ ID NO 3
<211> LENGTH: 15
<212> TYPE: DNA
<213> ORGANISM: Artificial sequence
<220> FEATURE:
<223> OTHER INFORMATION: oligonucleotide

<400> SEQUENCE: 3
aacgacaaaa cgaca                                                    15

<210> SEQ ID NO 4
<211> LENGTH: 18
<212> TYPE: DNA
<213> ORGANISM: Artificial sequence
<220> FEATURE:
<223> OTHER INFORMATION: oligonucleotide

<400> SEQUENCE: 4
ggaacgacaa aacgacaa                                                 18

<210> SEQ ID NO 5
<211> LENGTH: 21
<212> TYPE: DNA
<213> ORGANISM: Artificial sequence
<220> FEATURE:
<223> OTHER INFORMATION: oligonucleotide

<400> SEQUENCE: 5
gggggaacga caaaacgaca a                                             21